United States Patent [19]

Bennett et al.

[11] Patent Number: 5,154,170

[45] Date of Patent: Oct. 13, 1992

[54] OPTIMIZATION FOR RATE RESPONSIVE CARDIAC PACEMAKER

[75] Inventors: Tommy D. Bennett, Shoreview; Lucy M. Nichols, Maple Grove; Glenn M. Roline, David L. Thompson, all from Minn.

[73] Assignee: Medtronic, Inc., Minneapolis, Minn.

[21] Appl. No.: 567,476

[22] Filed: Aug. 14, 1990

[51] Int. Cl.⁵ .......................................... A61N 1/362
[52] U.S. Cl. ............................................. 128/419 PG
[58] Field of Search ................................ 128/419 PG

[56] References Cited

U.S. PATENT DOCUMENTS

| | | | |
|---|---|---|---|
| 4,428,378 | 1/1984 | Anderson et al. | 128/419 PG |
| 4,485,813 | 12/1984 | Anderson | 128/675 |
| 4,688,573 | 8/1987 | Alt | 128/419 PG |
| 4,722,342 | 2/1988 | Amundson | 128/419 PG |
| 4,782,836 | 11/1988 | Alt | 128/419 PG |
| 4,856,522 | 8/1989 | Hansen | 128/419 PG |
| 4,867,160 | 9/1989 | Schaldach | 128/419 PG |
| 4,867,161 | 9/1989 | Schaldach | 128/419 PG |
| 4,867,162 | 9/1989 | Schaldach | 128/419 PG |
| 4,901,726 | 2/1990 | Hansen | 128/419 PG |
| 4,940,052 | 7/1990 | Mann et al. | 128/419 PG |
| 4,966,146 | 10/1990 | Webb et al. | 128/419 PG |
| 4,972,834 | 11/1990 | Begemmann | 128/419 PG |
| 5,003,976 | 4/1991 | Alt | 128/419 PG |
| 5,016,632 | 5/1991 | Hoegnelid et al. | 128/419 PG |
| 5,044,365 | 9/1991 | Webb et al. | 128/419 PG |
| 5,063,927 | 11/1991 | Webb et al. | 128/419 PG |

FOREIGN PATENT DOCUMENTS

| | | |
|---|---|---|
| 0331309 | 2/1989 | European Pat. Off. |
| 0334675 | 3/1989 | European Pat. Off. |
| WO8906990 | 8/1989 | PCT Int'l Appl. |

OTHER PUBLICATIONS

PCT International Search Report, International Appln. No. PCT/US91/05746, International Filing Date Aug. 13, 1991, date of mailing Dec. 20, 1987 (4 pages), (PCT P-956).

*Primary Examiner*—Kyle L. Howell
*Assistant Examiner*—Scott M. Getzow
*Attorney, Agent, or Firm*—John A. Rissman; Harold R. Patton

[57] ABSTRACT

A rate responsive cardiac pacemaker for providing an optimized pacing rate of stimulation pulses as a function of at least one selected rate control parameter. Each rate control parameter has a value which varies as a function of changes in a patient's physiologic demand and includes a sensor system for sensing the rate control parameter value and for providing a sensor output representative thereof. The cardiac pacemaker also includes control circuitry which includes a rate response defining means for deriving desired pacing rates as a function of the sensor output and an achievement monitoring means that has a predetermined achievement criterion, for monitoring the relationship between the derived pacing rates and the achievement criterion over an optimization period. An output circuitry provides optimized pacing rates as a function of the desired pacing rates, such optimization being accomplished by adjusting the rate response function for each sensor as a function of of the monitored achievement relationship. Another optimization function is provided by adjusting a sensor weighting value which weights or regulates the relative contribution each sensor's derived desired pacing rates will contribute toward the pacemaker-derived optimized pacing rates, such sensor weighting value being adjusted as a function of the monitored achievement relationshp, or as a function of the sensor gain optimization activity, as desired.

7 Claims, 5 Drawing Sheets

OPTIMIZATION FOR RATE RESPONSIVE CARDIAC PACEMAKER

BACKGROUND OF THE INVENTION

1. Field of the Invention

The present invention generally relates to cardiac pacemakers, and more particularly, pertains to cardiac pacemakers of the type which measure physiologic or metabolic requirements and vary the rate of the pacemaker in accordance therewith.

2. Description of the Prior Art

Early cardiac pacemakers provided a fixed-rate stimulation pulse generator that could be reset on demand by sensed atrial and/or ventricular depolarizations. Modern pacemakers include complex stimulation pulse generators, sense amplifiers and leads which can be configured or programmed to operate in single or dual chamber modes of operation, delivering pacing stimuli to the atrium and/or ventricle at fixed rates or rates that vary between an upper rate limit and a lower rate limit.

In recent years, single and dual chamber pacemakers have been developed which measure rate control parameters (RCP's) which are directly or indirectly related to metabolic requirements (e.g., demand for oxygenated blood) and vary the pacing rate in response to such measured RCP's. Such RCP's include, for example, physical activity of the body, right ventricular blood pressure and the change of right ventricular blood pressure over time, venous blood temperature, venous blood oxygen saturation, respiration rate, minute ventilation, and various pre and post-systolic time intervals measured by impedance or pressure sensing within the right ventricle of the heart. Such RCP-measuring, sensor-driven pacemakers have been developed for the purpose of restoring rate response to exercise in patients lacking the ability to increase rate adequately by exertion.

In general, a rate responsive pacemaker includes a sensor which produces a sensor output representative of a selected RCP, such sensor output varying between a maximum sensor output level and a minimum sensor output level ("Sensor Output"). The pacemaker provides a pacing ("Pacing Rate") which typically varies as a linear or monotonic function ("f") of the sensor output between a selectable lower pacing rate ("Lower Rate") and upper pacing rate ("Upper Rate"). Function f has a selectable slope (i.e., Pacing Rate change/Sensor Output change) adjustable by means of an external programmer in conjunction with the Lower and Upper Rates. Thus, the Pacing Rate typically provided is equal to the pre-selected Lower Rate plus an increment which is a function of the measured Sensor Output, as follows:

Pacing Rate = Lower Rate + $f$(Sensor Output).

A human's heart rate, however, is normally controlled by a complex set of inputs to the autonomic nervous system. Consequently, no single type of sensor has been found to be entirely satisfactory for controlling rate response functions. Some of the shortcomings of single-sensor, rate responsive pacemakers, for example, can include: (1) long-term sensor instability, such as from degradation; (2) long-term changes in correlation between sensor output and its RCP being measured, due to physiologic changes in the patient, such as biologic/sensor interface changes due to tissue changes; (3) changes in sensor sensitivity; and (4) the need for frequent re-programming to accommodate the foregoing problems, as they are encountered.

Various efforts have consequently been made to develop a multiple-sensor pacemaker which is capable of varying its rate as a function of more than one type of measured RCP. Unfortunately, implementation of such multiple sensor-driven rate response concepts has proven to be very difficult and not entirely satisfactory. In addition to those problems listed above as to single-sensor pacemakers, other problems which are typically encountered include: (1) differences between sensors in long-term stability; (2) differences between sensors in immunity to noise; (3) differences in response time to changing metabolic conditions; (4) differences between sensors in correlation between each sensor output and its RCP being measured; and (5) complex set-up procedures, including the need for frequent re-programming.

Thus, a need exists for a rate response pacemaker which will better accommodate the above-identified problems, preferably in a self-adaptive manner, in the context of a single-sensor or multiple-sensor pacemaker.

SUMMARY OF THE INVENTION

The present invention provides a method and apparatus for automatically optimizing the packing rate in a rate-responsive cardiac pacemaker as a function of at least one selected rate control parameter (RCP), such that the above-listed problems are better accommodated in a self-adaptive manner. Each RCP has a value which varies as a function of changes in a patient's physiologic demand (such as for oxygenated blood).

The pacemaker of the present invention includes; (1) sensing means for sensing each RCP and for providing a sensor output representative of such RCP value; and (2) control circuitry coupled to sensing means, which includes, in addition to other functions listed below: (a) rate response defining means for deriving desired pacing rates as a function of each sensor output; (b) achievement monitoring means, having a predetermined achievement criterion, for monitoring the relationship between the derived desired pacing rates and the achievement criterion over a predetermined optimization period for each sensor; and (c) output means for providing optimized pacing rates as a function of said derived desired pacing rates, or as a function of a sensor weighting values (described below) or as a function of sensor gain optimization activity.

An optimization period is selected as an interval of time at the expiration of which various optimization functions are to be performed, such that the pacing rate is optimized during the subsequent optimization period.

An achievement criterion, such as a pacing rate, is initially selected for each sensor's corresponding range of desired pacing rates, such as a predetermined rate within such range. Achievement monitoring means provides an achievement output, such as an achievement count, which is indicative of the degree to which the desired pacing rates derived by rate response defining means are being achieved during a particular optimization period.

Two general types of apparatus and methods are provided for optimizing the rate of stimulus pulses provided by such pacemaker.

In one preferred embodiment, wherein an optimized pacing rate is provided by means of rate response or sensor gain being optimized, a pacemaker having one or more sensors includes rate response control means for adjusting the rate response function as a function of the achievement criterion. Following adjustment of the rate response functions or sensor gains at the expiration of each optimization period, during subsequent optimization periods the desired pacing rates being derived by the control circuitry, and thus the optimized pacing rate of pacemaker, can be expected to more adequately satisfy the particular patient's ongoing metabolic needs.

In another preferred embodiment, wherein an optimized pacing rate is provided by means of a sensor weighting being optimized, a pacemaker having two or more sensors includes sensor weighting control means for adjusting the sensor weighting value as a function of the achievement criterion. The sensor weighting value will weight the relative contribution which each sensor's desired pacing rates will contribute toward the pacemaker-derived optimized pacing rate. Following adjustment of the sensor weighting value at the end of each optimization period, during subsequent optimization periods the desired pacing rates being derived by the control circuitry, and thus the optimized pacing rate of pacemaker, can be expected to more adequately satisfy the particular patient's ongoing metabolic needs.

In another preferred embodiment, wherein both of the above optimization functions are combined, a pacemaker having two or more sensors provides an optimized pacing rate by performing the sensor gain optimization first, and then performing the sensor weighting optimization as a function of the sensor gain optimization activity performed. Following adjustment of both the sensor gains and sensor weighting value at the end of each optimization period, during subsequent optimization periods the desired pacing rates being derived by the control circuitry, and thus the pacemaker-derived optimized pacing rate of pacemaker which is a function of such adjusted sensor weighting value, can be expected to more adequately satisfy the particular patient's ongoing metabolic needs.

A significant advantage of the present invention is that each sensor's rate response will be automatically adjusted or optimized, depending upon the current gain setting's ability to achieve a pacing rate which meets the patient's ongoing metabolic needs. A further significant advantage of the present invention is that the weighting of each sensor-determined pacing rate will be automatically adjusted or optimized, depending upon the effectiveness of the sensor gain optimization, such that the pacemaker provides an optimized pacing rate to the patient. A primary benefit which flows directly from the foregoing relates to a significantly reduced need for, and frequency of, re-programming of the pacemaker, which yields both convenience and cost savings to the patient and corresponding clinical group. Other related benefits include: (1) better accommodation of differences, from patient to patient, in correlations between a particular sensor's output and the corresponding desired pacing rate; (2) better accommodation of differences, as to the same patient over time, in correlation between a particular sensor's output and the corresponding desired pacing rate due to physiological changes of the patient; and (3) better accommodation of differences in correlation between a particular sensor's output and the corresponding desired pacing rate due to device-related behavior, variability in components, sensor drift, etc.

BRIEF DESCRIPTION OF THE DRAWINGS

The present invention will be better understood, and its attendant advantages will be readily appreciated, by reference to the accompanying drawings when taken in consideration with the following detailed description, wherein.

DETAILED DESCRIPTION OF THE PREFERRED EMBODIMENTS

Part I. Description of Pacemaker Device

Figure 1:
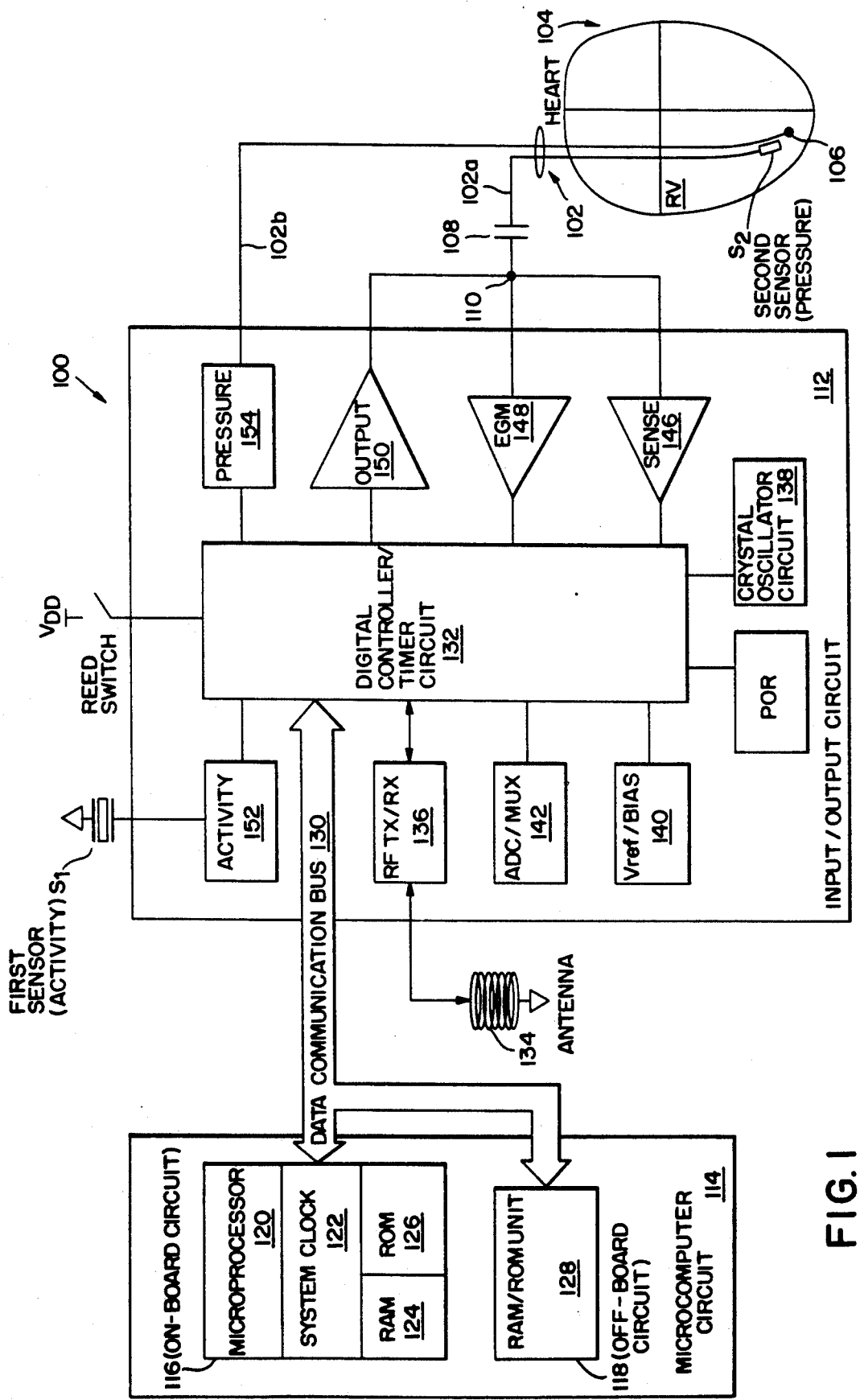
FIG. 1 is a block circuit diagram of an multi-sensor, rate-responsive, implantable, single-chamber, cardiac pacemaker having automatic rate response optimization according to the present invention.

FIG. 1 is a block circuit diagram illustrating a multi-programmable, implantable, single-chamber, bradycardia pacemaker 100 with multi-sensor rate variability and automatic rate response optimization according to the present invention. Although the present invention is described in conjunction with a microprocessor-based architecture, it will be understood that it could be implemented in digital logic-based, custom IC architecture, if desired. It will also be understood that the present invention may be implemented in dual-chamber pacemakers.

In the preferred embodiment of FIG. 1, pacemaker 100 includes two sensors, namely, $S_1$ and $S_2$, each of which provide a sensor output which varies as a function of a measured parameter that relates to the metabolic requirements of the patient. Since each sensor output can be utilized by pacemaker 100 to control its pacing rate, each sensor output is herein referred to as a rate-control parameter (RCP). Examples of an RCP include, for example, physical activity of the body, right ventricular blood pressure and the change of right ventricular blood pressure over time, venous blood temperature, venous blood oxygen saturation, respiration rate, minute ventilation, and various pre and post-systolic time intervals measured by impedance or pressure sensing within the right ventricle of the heart.

In the preferred embodiment, first sensor $S_1$ comprises an activity sensor, such as a piezoelectric sensor of the type disclosed in U.S. Pat. No. 4,428,378 issued to Anderson et al., entitled "Rate Adaptive Pacer", which is held by the same assignee as the present invention and which is incorporated herein by reference. First sensor $S_1$ thus measures a rate-control parameter related to physiologic forces associated with body activity ($RCP_{act}$), and provides a first sensor output ($Output_{act}$) which is proportional to the patient's activity. Also in the preferred embodiment, second sensor $S_2$ comprises a dynamic pressure sensor, such as the type disclosed in U.S. Pat. No. 4,485,813 issued to Anderson et al., entitled "Implantable Dynamic Pressure Transducer System", which is held by the same assignee as the present invention and which is incorporated by herein by reference. Second sensor $S_2$ thus measures a rate-control parameter related to changes in fluid pressure in the heart associated with its mechanical activity and contractility ($RCP_{press}$), and provides a second sensor output ($Output_{press}$) which is proportional to the magnitude of the change in fluid pressure in the patient's heart. In the preferred embodiment, second sensor $output_{S2}$ is processed to derive a peak positive time derivative of the fluid pressure applied to the pressure sensor $S_2$ within the right ventricle of the patient's heart (i.e., $dP/dt_{max}$).

Pacemaker 100 is schematically shown electrically coupled via a pacing lead 102 to a patient's heart 104. Lead 102 includes an intracardiac electrode 106 and second sensor $S_2$ which are located near the distal end of lead 102 and positioned within the right ventricle (RV) of the patient's heart. Lead 102 can carry either unipolar or bipolar electrodes as is well known in the art. In the preferred embodiment, the lead 102 which couples pacemaker 100 to the ventricular endocardium can comprise a steroid-tipped, unipolar lead with an integral pressure transducer of the type described above. Electrode 106 is coupled via suitable lead conductor 102a through output capacitor 108 to node 110 and to input/output terminals of an Input/Output Circuit shown at block 112. Output from first sensor $S_1$ is coupled to Input/Output Circuit 112. Output from second sensor $S_2$ is also coupled to Input/Output Circuit 112 via suitable lead conductor 102b.

Input/Output Circuit 112 contains the operating input and output analog circuits for digital controlling and timing circuits necessary for the detection of electrical signals derived from the heart, such as the cardiac electrogram, output from the first sensor output $S_1$, and output from the second sensor output $S_2$, as well as for the application of stimulating pulses to the heart to control its rate as a function thereof under the control of software-implemented algorithms in a Microcomputer Circuit shown at 114.

Microcomputer Circuit 114 comprises an On-Board Circuit 116 and an Off-Board Circuit 118. On-Board Circuit 116 includes a microprocessor 120, a system clock 122, an don-board RAM 124 and ROM 126. Off-Board Circuit 118 includes an off-board RAM/ROM Unit 128. Micromputer Circuit 114 is coupled by Data Communication Bus 130 to a Digital Controller/Timer Circuit shown at 132. Microcomputer Circuit 114 may be fabricated of custom IC devices augmented by standard RAM/ROM components.

It will be understood that the electrical components represented in FIG. 1 are powered by an appropriate implantable-grade battery power source (now shown).

An antenna 134 is connected to Input/Output Circuit 112 for purposes of uplink/downlink telemetry through an RF Transmitter/Receiver Circuit (RF TX/RX) shown at 136. Telemetering both analog and digital data between antenna 134 and an external device, such as an external programmer (not shown), is accomplished in the preferred embodiment by means of all data first being digitally encoded and the n pulse position modulated on a damped RF carrier, as substantially described in co-pending U.S. patent application Ser. No. 468,407, filed on Jan. 22, 1990, entitled "Improved Telemetry Format", which is held by the same assignee as the present invention and which is incorporated herein by reference.

A Crystal Oscillator Circuit 138, typically a 32,768 Hz crystal-controlled oscillator, provides main timing clock signals to Digital Controller/Timer Circuit 132. A Vref/Bias Circuit 140 generates a stable voltage reference and bias currents for the analog circuits of Input/Output Circuit 112. An ADC/Multiplexor Circuit (ADC/MUX) 142 digitizes analog signals and voltages to provide telemetry and replacement time-indicating function (EOL). A Power-on-Reset Circuit (POR) 144 functions as a means to reset circuit and related functions to a default condition upon detection of a low battery condition, which will occur upon initial device power-up or transiently occur in the presence of electromagnetic interference, for example.

The operating commands for controlling the timing of the pacemaker depicted in FIG. 1 are coupled by bus 130 to Digital Controller/Timer Circuit 132 wherein digital timers set the overall escape interval of the pacemaker, as well as various refractory, blanking and other timing windows for controlling the operation of the peripheral components within Input/Output Circuit 132.

Digital Controller/Timer Circuit 132 is coupled to a sense amplifier (SENSE) 146 and an electrogram amplifier (EGM) 148 for receiving amplified and processed signals picked up from electrode 106 through lead conductor 102a and capacitor 108 representative of the electrical activity of the patient's heart 104. SENSE amplifier 146 produces a sense event signal for re-setting the escape interval timer within Circuit 132. The electrogram signal developed by EGM amplifier 148 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention and which is incorporated by herein by reference. An output pulse generator 150 provides the pacing stimulus to the patient's heart 104 in response to a paced trigger signal developed by Digital Controller/Timer Circuit 132 each time the escape interval times out, or an externally transmitted pacing command has been received, or in response to other stored commands as is well known in the pacing art.

Digital Controller/Timer Circuit 132 is coupled to a processing/amplifying circuit (ACTIVITY) 152 for receiving amplified and processed sensor output ($Output_{act}$) from first sensor $S_1$ and associated ACTIVITY circuitry which is representative of activity. Digital Controller/Timer Circuit 132 is coupled to a processing/amplifying circuit (PRESSURE) 154 for receiving amplified and processed sensor output (Output$_{press}$) from second sensor S$_2$ through lead conductor 102b representative of changes in fluid pressure in the patient's heart 104, for use in rate response control, and others functions as desired.

In a preferred embodiment of the present invention, pacemaker 100 is capable of operating in various non-rate-responsive modes which include VVI, VOO and VVT, as well as corresponding rate-responsive modes of VVIR, VOOR and VVTR. Further, pacemaker 100 can be programmably configured to operate such that it varies its rate only in response to one selected sensor output, or in response to both sensor outputs, if desired (i.e., utilizing either or both of Output$_{act}$ or Output$_{press}$).

Part II. Definitions

For purposes of describing this invention, a definition of additional relevant terms follows:

Achievement Count (ACH.COUNT)—A measure of the attainment of an Achievement Criterion (ACH.-CRITERION) by the Sensor Target Rate (STR) associated with each RCP-measuring sensor over a predetermined time interval which comprises the Optimization Period (OPT.PERIOD).

Achievement Criterion (AC.CRITERION)—A value supplied by the clinician which sets an attainment threshold for each Sensor Target Rate (STR) associated with each sensor. This threshold comprises a rate component (Achievement Rate) and a time component (Achievement Duration). The Achievement Rate is a programmable percentage of the difference between the Lower Rate (LR) and the Upper Rate (UR). The Achievement Duration is a minimum time interval over which the Sensor Target Rate must exceed the Achievement Rate. With rate response, the allowed programmable values for ACH.CRITERION range from 70 ppm to 175 ppm at 1 ppm intervals, and the Achievement Duration in the preferred embodiment is fixed at a four-second interval.

Activity Count (ACT.COUNT)—A measure of the output of the activity sensor (Output$_{act}$) over a predetermined interval of time. In the preferred embodiment, each event in which the amplitude of Output$_{act}$ exceeds a predetermined Activity Threshold (ACT.THRESH) is counted over a two-second period and retained. ACT.COUNT is updated every two-second cycle, and its aggregate value comprising the count value accumulated at the end of 3 two-second cycles (i.e., after 6 seconds) is used to calculate the Sensor Target Rate for activity (STR$_{act}$).

Activity Rate Response Gain (ACT.GAIN)—A setting which corresponds to the slope of the function correlating the activity-based Sensor Target Rate (STR$_{act}$) to a value (ACT.COUNT) which corresponds to the activity sensor output (Output$_{act}$). The setting for ACT.GAIN, sometimes alternately referred to as the "activity sensor gain", corresponds to a particular rate response curve (RR). With rate response, the allowed programmable values for ACT.GAIN range from 1 to 10 at setting intervals of 1 (i.e., from RR1 to RR10).

Activity Response Time Acceleration Constant (ACT.ATTACK.TC)—A value which restricts the rate at which the activity-based Sensor Target Rate (STR$_{act}$) rate can increase, such that an activity "attack" curve provides for a more gradual and physiologically appropriate change in pacing rate. In the preferred embodiment, these time values represent the time required to reach 90% of the difference between a first steady-state activity-driven pacing period (constant activity signal input for at least a six-second interval) and a second, shorter, steady-state, activity-driven pacing period when a step increase in activity level occurs. With rate response, the allowed programmable values for ACT.ATTACK.TC are selected from those of 0.25 minutes, 0.5 minutes, or 1.2 minutes.

Activity Response Time Deceleration Constant (ACT.DECAY.TC)—A value which restricts the rate at which the activity-based Sensor Target Rate (STR$_{act}$) can decrease, such that an activity "decay" curve provides for a more gradual and physiologically appropriate change in pacing rate. In the preferred embodiment, these time values represent the time required to reach 90% of the difference between a first steady-state activity-driven pacing period (constant activity signal input for at least a six-second interval) and a second, longer, steady-state, activity-driven pacing period when a step decrease in activity level occurs. With rate response, the allowed programmable values for ACT.DECAY.TC are selected from those of 2.5 minutes, 5 minutes, or 10 minutes.

Activity Threshold (ACT.THRESH)—A minimum value which the amplitude of the activity sensor output (Output$_{act}$) must exceed to serve as input to the rate determination algorithm. The higher the threshold, the greater the amplitude necessary to become an event counted in the Activity Count (ACT.COUNT). With rate response, the allowed programmable values for ACT.THRESH range from low, medium low, medium, medium high, and high.

Lower Rate (LR)—A value supplied by the clinician which establishes a lower boundary on the pacing rate. If the sensors are disabled, or their sensor outputs are not large enough to increase rate, the lower rate is the stimulus rate. With rate response, the allowed programmable values for LR range from 40 ppm to 100 ppm at 1 ppm intervals.

Optimization Period (OPT.PERIOD)—A predetermined time interval, after which the pacemaker 100 performs its optimization of each sensor's rate response (ACT.GAIN or PRESS.GAIN) and Weighting Coefficient (COEFF), based upon the ACH.COUNT value relative to the OPT.RANGE at the expiration of each OPT.PERIOD. In the preferred embodiment, the OPT.PERIOD is established to be a twenty-four hour period.

Optimization Range (OPT.RANGE)—A range determined by the pacemaker 100 as a function of a value (Achievement Index) supplied by the clinician, which defines a minimum value (OPT.RANGE.MIN) and a maximum value (OPT.RANGE.MAX) for the Achievement Count (ACH.COUNT) during each Optimization Period (OPT.PERIOD). With rate response, the allowed programmable values for Achievement Index range from 3 to 8 at setting intervals of 1. In the preferred embodiment, pacemaker 100 determines OPT.RANGE by calculating the minimum value (OPT.RANGE.MIN) by subtracting 2 from the Achievement Index and its maximum value (OPT.RANGE.MAX) by adding 2 to the Achievement Index. Optimization for each sensor's rate response (ACT.GAIN or PRESS.GAIN) and Weighting Coefficient (COEFF) are performed by pacemaker 100 based upon the ACH.COUNT value relative to the OPT.RANGE at the expiration of each OPT.PERIOD.

Optimized Pacing Rate (OPR)—The rate at which the pacemaker 100 is to provide stimulus pulses, which is derived by pacemaker 100 based upon the Sensor Pacing Rates ($SPR_{act}$ and $SPR_{press}$) and the Weighting Coefficient (COEFF), based upon Equation 1 hereinbelow described in Part II.

Pressure (dP/dt) Average (PRESS.AVG)—Dynamic pressure sensor $S_2$ is disposed in the right ventricle (RV) of the patient's heart to sense fluid pressure therein ($RCP_{press}$), and to provide a sensor output ($Output_{press}$) related to changes in the fluid pressure associated with the heart's mechanical activity and contractility. Processing by pacemaker 100 of $Output_{press}$ yields a peak positive fist time derivative thereof ($dP/dt_{max}$) which is proportional to the magnitude of such RV pressure changes. Each sensed or paced RV event will yield a peak positive $dP/dt_{max}$ signal, although a peak negative signal may be used as an alternative. In the preferred embodiment, the last 8 valid $dP/dt_{max}$ values are used to determine an average $dP/dt_{max}$ value, referred to as the "Pressure (dP/dt) Average" or "PRESS.AVG". Pacemaker 100 tests for validity of each $dP/dt_{max}$ value on a sample-by-sample basis, based upon the requirement that a sampled $dP/dt_{max}$ value must be within a predetermined range defined by a $dP/dt_{max}$ value (REST.PRESS) associated with the patient's Resting Rate (REST.RATE). In the preferred embodiment, this validity range is defined as $dP/dt_{max}$ values between 25% to 400% of REST.PRESS. Values outside this validity range are ignored. Once determined, PRESS.AVG is used to calculate the pressure-based Sensor Target Rate ($STR_{press}$) on a cycle-to-cycle basis or once upon request, according to Equation 3 hereinbelow set forth.

Pressure (dP/dt) Rate Response Gain (PRESS.GAIN)—A setting which corresponds to the slope of the function correlating the pressure-based Sensor Target Rate ($STR_{press}$) to a value (PRESS.AVG) which corresponds to the pressure sensor output ($Output_{press}$). The setting for PRESS.GAIN, sometimes alternately referred to as the "pressure sensor gain" or "dP/dt sensor gain", corresponds to a particular rate response curve (RR). With rate response, the allowed programmable (permanent) values for PRESS.GAIN range from 1 to 10 at setting intervals of 1 (i.e., from RR1 to RR10).

Pressure (dP/dt) Response Time Acceleration Constant (PRESS.ATTACK.TC)—A value which restricts the rate at which the pressure-based Sensor Target Rate ($STR_{press}$) can increase, such that a pressure "attack" curve provides for a more gradual and physiologically appropriate change in pacing rate. In the preferred embodiment, this time value represents the time required to reach 90% of the difference between a first steady-state, pressure-driven pacing period (constant $dP/dt_{max}$ signal input for at least 8 events) and a second, shorter, steady-state, pressure-driven pacing period when a step increase in $dP/dt_{max}$ level occurs. With rate response, PRESS.ATTACK.TC has a fixed value of 0.25 minutes.

Pressure (dP/dt) Response Time Deceleration Constant (PRESS.DECAY.TC)—A value which restricts the rate at which the pressure-based Sensor Target Rate ($STR_{press}$) can decrease, such that a pressure "decay" curve provides for a more gradual and physiologically appropriate change in pacing rate. In the preferred embodiment, this time value represents the time required to reach 90% of the difference between a first steady-state, pressure-driven pacing period (constant $dP/dt_{max}$ signal input for at least 8 events) and a second, longer, steady-state, pressure-driven pacing period when a step decrease in $dP/dt_{max}$ level occurs. With rate response, PRESS.DECAY.TC has a fixed value of 0.25 minutes.

Resting (dP/dt) Pressure (REST.PRESS)—The arithmetic mean of the pressure-based signal of interest (peak positive dP/dt values or $dP/dt_{max}$) measured during a predefined time interval with the patient at rest (i.e., the representative $dP/dt_{max}$ value which correlates to REST.RATE).

Resting Rate (REST.RATE)—A rate identified by the clinician during initialization for later use in the pressure-based pacing mode comprising the arithmetic mean of paced or intrinsic rates measured over a predefined time interval with the patient at rest. In the preferred embodiment, the allowed programmable values for REST.RATE range from 40 ppm to 100 ppm at 5 ppm intervals.

Sensor Pacing Rate (SPR)—The rate calculated by the pacemaker 100 in conjunction with each sensor based upon its respective Sensor Target Rate (STR) and the contribution thereto based upon its respective acceleration and deceleration function.

Sensor Target Rate (STR)—The rate calculated by the pacemaker 100 in conjunction with each sensor based upon programmed settings and the respective sensor output. STR does not take into account the effect which the acceleration and deceleration function produce on the Sensor Pacing Rate (SPR).

Upper Rate (UR)—A value supplied by the clinician which limits the maximum stimulation rate when the rate responsive modes for activity, pressure, or both combined, are in effect, such that the sensor-driven pacing rate generated by pacemaker 100 does not become hemodynamically excessive. With rate response, the allowed programmable values range from 100 ppm to 175 ppm at 5 ppm intervals, provided UR must also be at least 20 ppm greater than Lower Rate (LR) and Resting Rate (REST.RATE).

Weighting Coefficient (COEFF)—In a rate-response pacing mode wherein both sensors (i.e., more than one sensor) are enabled, the "Weighting Coefficient" establishes the proportion or weight of control given to each Sensor Pacing Rate (SPR) in deriving a fully-optimized rate (Optimized Pacing Rate) at which the pacemaker 100 should provide stimulus pulses (OPR). After each STR has been calculated as an intermediate rate control value from its respective Sensor Target Rate (STR), the coefficient is used in a weighting equation as a form of gain multiplier to regulate the emphasis placed on each STR in order to derive the Optimized Pacing Rate (OPR) at which the pacemaker 100 can deliver stimulus pulses. In the preferred embodiment, an OPR is calculated as follows:

$$OPR = [(1 - COEFF)*SPR_{act}] + (COEFF*SPR_{press}) \quad \text{(Equation 1)}$$

During initialization by the programmer, a Programmed Coefficient Value ($COEFF_{PROG}$) is also assigned by the programmer, such as a value of 0.5, to which pacemaker 100 will automatically default upon the occurrence of certain events encountered during an optimization procedure, as hereinbelow described. In the preferred embodiment, the allowed programmable values for COEFF range from 0 to 1.0 at interval settings of 0.125. During an optimization cycle at the end of the OPT.PERIOD, pacemaker 100 can automatically adjust COEFF by a step increment or decrement of 0.125, or in larger increments or decrements in a single optimization cycle under certain conditions hereinbelow described.

Part III. Sensors

A brief description of measurement of the rate control parameter for activity ($RCP_{act}$) now follows. The activity sensor $S_1$ sensor employed is a piezoelectric crystal transducer of the type described in the above-mentioned '378 Anderson et al. patent, which is mounted to the interior surface of the pacemaker can as disclosed therein. Sensor $S_1$ generates a sensor output ($Output_{act}$) due to deflection of the pacemaker can as a result of compression waves within the body caused by physical movement of the body. Processing by ACTIVITY circuit 152 is performed, such that each event in which the amplitude of $Output_{act}$ exceeds a programmed Activity Threshold (ACT.THRESH) is then counted and retained in an Activity Count (ACT.COUNT) of pacemaker 100. ACT.COUNT is used to calculate the activity-based Target Rate ($STR_{act}$) on a cycle-to-cycle basis, according to Equation 3 hereinbelow set forth in Part IV.

A brief description of measurement of the rate control parameter for pressure ($RCP_{press}$) now follows. The pressure sensor $S_2$ sensor employed is a dynamic pressure sensor of the type described in the above-mentioned '813 Anderson et al. patent. Sensor $S_2$ is disposed in the right ventricle (RV) of the patient's heart to sense fluid pressure therein ($RCP_{press}$), and to provide a sensor output ($Output_{press}$) related to changes int he fluid pressure associated with the heart's mechanical activity and contractility. Processing by PRESSURE circuit 154 of $Output_{press}$ yields a peak positive first time derivative thereof ($dP/dt_{max}$) which is proportional to the magnitude of such RV pressure changes. Each sensed or paced RV event will yield a peak positive $dP/dt_{max}$ signal, although a peak negative signal may be used as an alternative. In the preferred embodiment, the last 8 valid $dP/dt_{max}$ values are used to determine an average $dP/dt_{max}$ value, referred to as the "Pressure (dP/dt) Average" or "PRESS.AVG". Pacemaker 100 tests for validity of each $dP/dt_{max}$ value on a sample-by-sample basis, based upon the requirement that a sampled $dP/dt_{max}$ value must be within a predetermined range defined by a $dP/dt_{max}$ value (REST.PRESS) associated with the patient's Resting Rate (REST.RATE). In the preferred embodiment, this validity range is defined as $dP/dt_{max}$ values between 25% to 400% of REST.PRESS. Values outside this validity range are ignored. Once determined, PRESS.AVG is sued to calculate the pressure-based Sensor Target Rate ($STR_{press}$) on a cycle-to-cycle basis, according to Equation 3 hereinbelow set forth in Part IV.

It will be understood, however, that the present invention can be practiced with more than two sensors, or with sensors of a type other than the ones above described. In the preferred embodiment, however, various advantages are obtained by the use of the particular sensors in the specific combination stated above.

For example, an activity-based sensor provides a fast and repeatable response to physical activity. Sensors of this type have been exhaustively reported in clinical literature, and their safety and efficacy are well-documented. Additionally, such sensors offer the advantage of being less affected by changes in a patient's health or disease status, and thus provide more predictable behavior over time. However, there are also theoretical and practical limitations to the behavior of activity sensors. For example, they respond only to physical activity. Therefore, patients undergoing other types of physiological stresses which would normally evoke a heart rate response, such as thermal stress associated with normal exposure to wide variations in ambient temperature, or postural stress associated with changing from lying down to erect position, will tend to obtain only very limited rate adjustment and their adjustment to such stresses will thus be less than entirely adequate. Additionally, the time course of rate recovery after an activity event tends to be limited by the design constraints of the pacemaker system which are not generally capable of providing a highly physiologically-based recovery function.

Consequently, the preferred embodiment also incorporates a dynamic pressure sensor for continuous measurement of cardiac pressures on a beat-by-beat basis. This sensor provides for more physiological responses than activity alone, and helps to complement the rate response provided by the activity sensor. The sensed physiologic variable in this system comprises the rate of increase in pressure within the right ventricle of the heart (i.e., a peak positive dP/dt). This variable is related to the vigor of contraction of the cardiac muscle, which in turn is regulated by the autonomic nervous system. Thus, any stress which elicits a response by the autonomic nervous system in the patient (and would cause a heart rate response in a normal individual), will also yield a heart rate response in the patient by means of the pacemaker system of the present invention. Additionally, the time course of recovery of the cardiac pressure following stresses follows the physiologic time course determined by the status of the autonomic nervous system, such that the present device will provide for pacing rate recovery which is more physiological than that which can be provided by activity sensors alone.

It can thus be appreciated that the particular sensor combination described above yields significantly improved rate response function for pacemaker 100.

Part IV. Rate Response (Sensor Gain) Curves

Figure 2A:
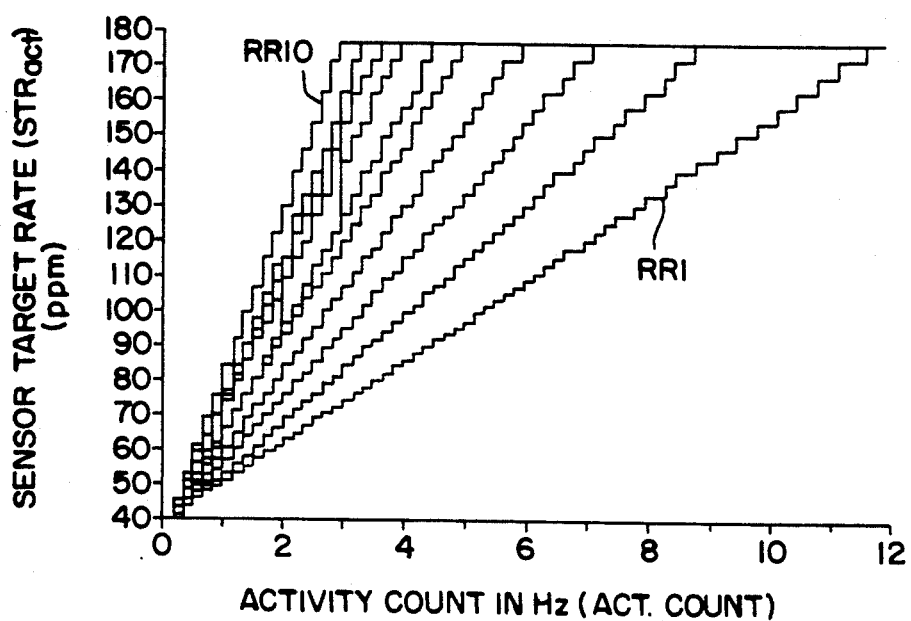
FIG. 2A is a graph illustrating multiple rate response curves correlating an output derived from a first sensor (which measures an activity-based rate control parameter) with a target pacing rate (calculated as a function of such first sensor output)
Figure 2B:
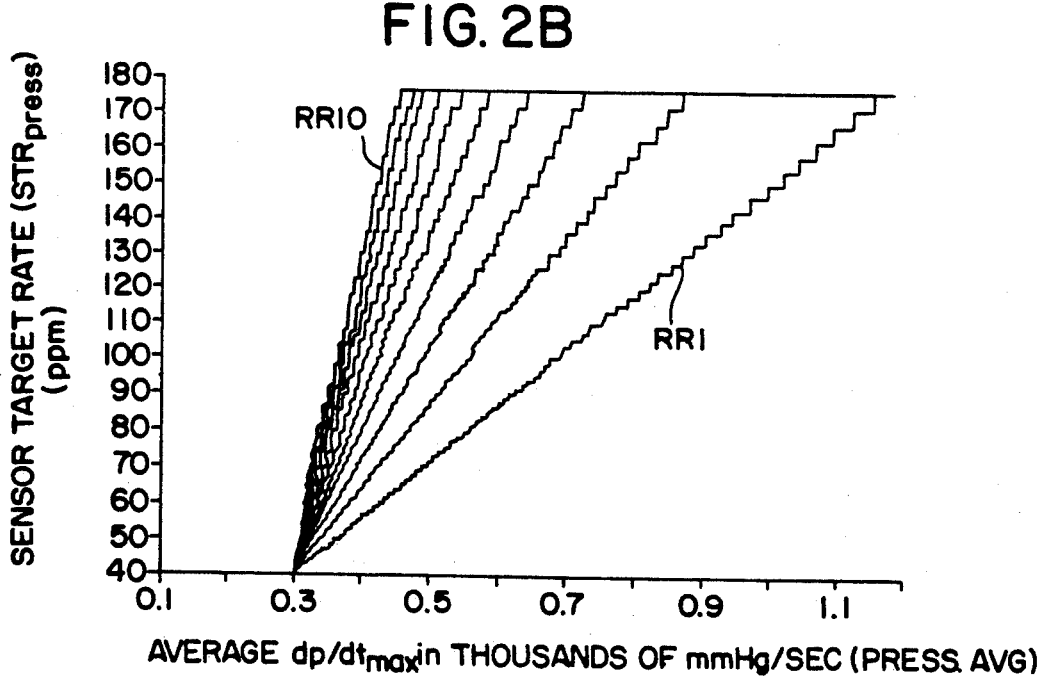
FIG. 2B is a graph illustrating multiple rate response curves correlating an output derived from a second sensor (which measures a pressure-based rate control parameter) with a target pacing rate (calculated as a function of such second sensor output)

FIGS 2A and 2B each graphically illustrate examples of a family of rate response curves for the first and second sensors $S_1$ and $S_2$, respectively. The horizontal axes of each graph correspond to sensor output values being measured. In FIG. 2A, the metric for the horizontal axis corresponds to an activity-based rate control parameter ($RCP_{act}$) and comprises the Activity Count (ACT.COUNT) as defined above, which is a function of $Output_{act}$, expressed in counts per second (Hz). In FIG. 2B, the metric for the horizontal axis corresponds to a pressure-based rate control parameter ($RCP_{press}$) and comprises the average $dP/dt_{max}$ value determined (PRESS.AVG) as defined above, which is a function of $Output_{press}$, expressed in thousands of mmHg per second. The vertical axes of each graph correspond to a Sensor Target Rate (STR), expressed in pulses per minute (ppm).

It can be seen that the Sensor Target Rate (STR) for each sensor is thus a function of the respective sensor's output, which functional correlation is defined in more detail hereinbelow. These Sensor Target Rates are utilized by pacemaker 100 in deriving the rate-responsive pacing rate for the patient's heart.

Ten rate response functions are established for each sensor, such that each function provides for excursion between selected lower and upper pacing rates within the available range of sensor outputs corresponding therewith. Multiple rate response functions are provided to afford the necessary flexibility in providing alternative rate response settings to accommodate for various factors, such as: (a) group-based correlation drift wherein differences exist among a group of patients regarding their respective correlations between the sensor output and corresponding desired pacing rate; (b) individual-based correlation drift wherein the sensor output associated with the rate control parameter being measured does not remain constant over the life of the pacemaker for an individual patient primarily due to physiological changes of the patient over time, such as due to aging; and (c) non-physiological-based correlation drift wherein the sensor output associated with the rate control parameter being measured does not remain constant over the life of the pacemaker sensor primarily due to pacemaker performance changes, such as drift in sensor output.

The various rate response functions shown in FIGS. 2A and 2B are established in conjunction with programmable parameters provided by the patient's physician using an external programmer, in a manner which is generally similar to that described in two co-pending U.S. patent applications, namely, U.S. patent application Ser. No. 455,717, filed on Dec. 22, 1989, entitled "Method and Apparatus for Implementing Activity Sensing in a Pulse Generator", and U.S. patent application Ser. No. 549,568, filed on Jul. 6, 1990, entitled "Programming Non-Volatile Memory Through Hermetic Feedthrough", which are held by the same assignee as the present invention and which are incorporated herein by reference.

The target rates for each rate control parameter are determined as follows:

(Equation 2): ACTIVITY SENSOR ($S_1$): $STR_{act} =$ $$\frac{(ACT \cdot COUNT + D)}{C} * K$$

(Equation 3): PRESSURE SENSOR ($S_2$): $STR_{press} =$ $$\frac{(PRESS \cdot AVG + B)}{A} * K$$

In the above equations, $K=(32{,}768*60/328)$ and is a constant to convert clock cycle, time interval-based data to rate-based data (ppm) and A, B, C, and D constitute variables which are derived from programmed values provided by the external programmer during initialization.

Numerous programmable parameters, for example, will be established during initialization of pacemaker 100, which is described in co-pending U.S. Pat. Appln., filed on even date herewith, entitled "Rate Responsive Pacemaker and Method for Automatically Initializing the Same", by Bennett et al., which is held by the same assignee as the present invention and which is incorporated herein by reference. More specifically, variables A, B, C, and D are a function of the programmed Upper Rate (UR), Lower Rate (LR), and the respective rate response gain parameters (ACT.GAIN and PRESS.GAIN, for specific sensors, or RR in general), Resting Rate (REST.RATE), Resting dP/dt) pressure (REST.PRESS), and determine the shape desired for the various rate response curves illustrated, for example, in FIGS. 2A and 2B. Pacemaker 100 includes an arithmetic logic unit (ALU) capable of generating A, B, C and D values as a function of such programmed parameters, and for making the necessary calculations to generate the respective sensor target rates and controlling the pacemaker rate as a function thereof.

In the rate response graphs of FIGS. 2A and 2B, for example, a range of Target Rates extends between a Lower Rate (FIG. 2A) or a Resting Rate (FIG 2B) of 40 ppm, and an Upper Rate of 175 ppm. Settings for rate response gain (ACT.GAIN and PRESS.GAIN for specific sensors, or RR in general) range from 1 to 10. It can be seen, for example, that the same magnitude of change in measured sensor output yields the greatest incremental change in target pacing rate under RR10, in contrast to the least incremental change in target pacing rate under RR1. The correlation thus defined between the sensor output and target pacing rate under these rate response curves is also often referred to as the "sensor gain function", wherein RR10 provides highest gain and RR1 provides lowest gain.

Each time the physician alters the selected values for UR, LR RR, REST.RATE and REST.PRESS via telemetry from the external programmer, these updated values are loaded into the program registers of pacemaker 100, such that new A, B, C and D values which are subsequently generated by the pacemaker 100 may be utilized by it in controlling the pacing rate as a function thereof. Regardless of which of the selected parameters has changed, the resulting function relating the Sensor Target Rate (STR) to sensor output, will take the basic form, extending from the Lower Rate (LR), or Resting Rate (REST.RATE) as appropriate, corresponding to a minimal sensor output, to the Upper Rate (UR) corresponding to an expected maximum sensor output, with a sensor output required to achieve UR decreasing as the rate response setting (RR) is increased.

The programmer also includes means for selection of acceleration and deceleration parameters which limit the rate of change in pacing rate on onset and cessation of activity, such as pacemaker 100 calculating the Sensor Pacing Rate (SPR) for each sensor as a function of its respective Sensor Target Rate (STR) and the contribution thereto based upon its respective acceleration and deceleration function. Typically, these acceleration and deceleration parameters are referred to in rate-responsive pacemakers as the attack or decay setting, respectively. These may be expressed as the time interval required for the pacemaker to change between the current pacing interval and 90% of the desired pacing interval, assuming that the physiologic stress level corresponding to the desired pacing rate remains constant, such as provided by ACT.ATTACK.TC, ACT.DECAY.TC, PRESS.ATTACK.TC and PRESS.DECAY.TC in the preferred embodiment. A more detailed description of the use of the above-described attack/decay settings in conjunction with pacemaker 100, including a modified decay feature which provides a pacing rate which decelerates at more than one decay time constant, is described in co-pending U.S. Pat. Appln., filed on even date herewith, entitled "Rate Responsive Pacemaker and Pacing Method", which is held by the same assignee as the present invention and which is incorporated herein by reference.

Part V. Achievement Criterion

Figure 3:
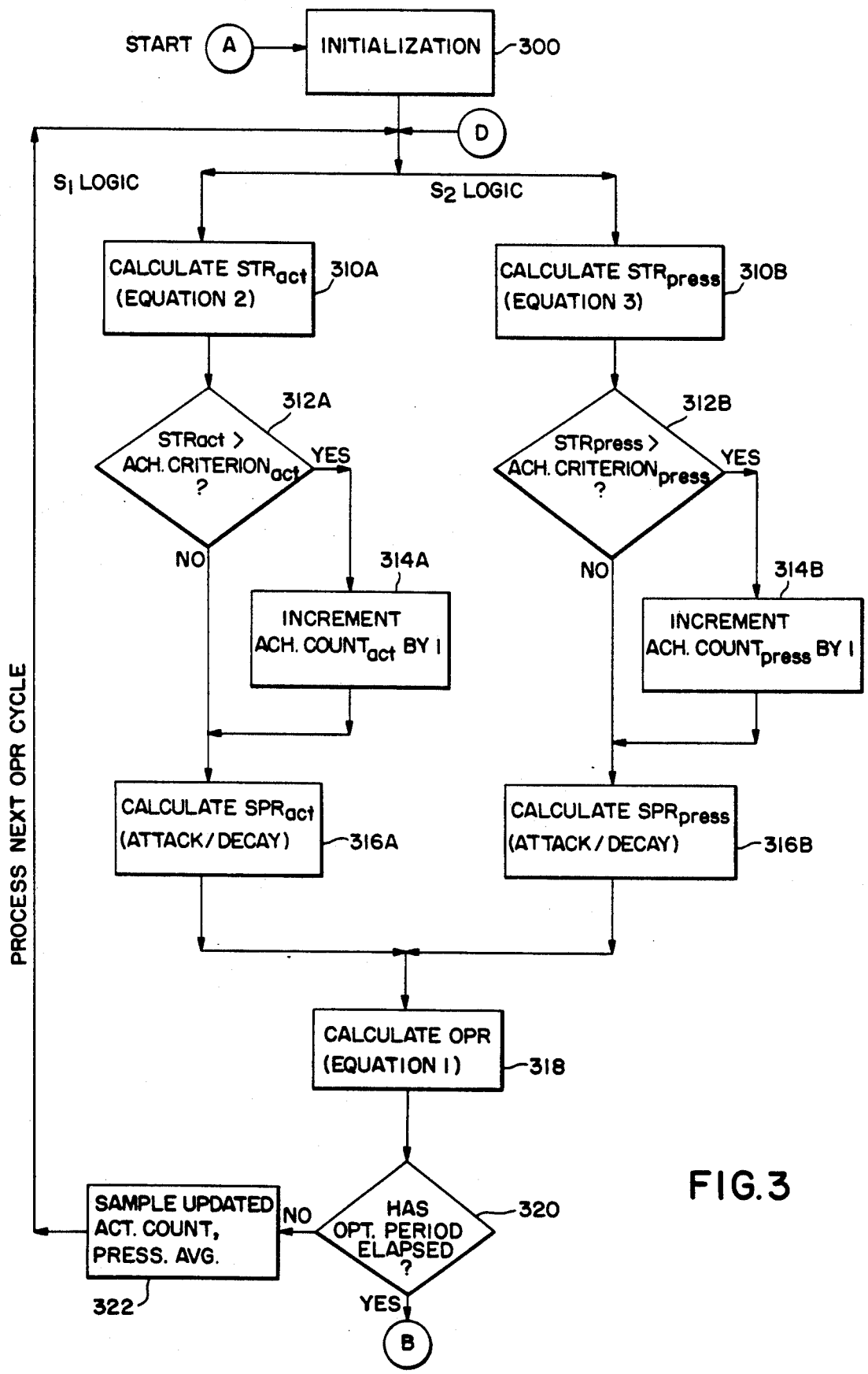
FIG. 3 is a simplified flowchart showing the basic function of software of the pacemaker of FIG. 1 for monitoring the attainment of achievement criterion for each of its sensors and for calculating an optimzied pacing rate as a function thereof.

FIG. 3 is a simplified flowchart showing the basic function of software for monitoring the attainment of the Achievement Criterion by a pacemaker having at least two sensors of the type hereinabove described. It will be understood, however, that the software logic described in FIG. 3 is applicable to pacemakers having one, two or more sensors, for which an optimization of rate response as a function of an Achievement Criterion is desired.

Entering the flowchart at starting position A, block 300 corresponds to the initialization routine. At this time, the physician-selected parameters are established and programmed into storage registers in pacemaker 100 (FIG. 1) using conventional programming techniques, as hereinabove described. Various counters and flags associated with the various optimization procedures according to the present invention, which are hereinbelow described in connection with FIGS. 4 and 5, will also be initialized to the appropriate values at this time.

The remainder of FIG. 3 generally illustrates the software logic for a rate responsive pacemaker having two sensors, $S_1$ (sensing activity) and $S_2$ (sensing pressure), for purposes of monitoring the attainment of Achievement Criterion (ACH.CRITERION$_{act}$ and ACH.CRITERION$_{press}$) by each sensor's associated Sensor Target Rate (STR$_{act}$ and STR$_{press}$), throughout the duration of the Optimization Period (OPT.PERIOD). The left-hand side of FIG. 3 generally corresponds to the logic associated with $S_1$ by which its Achievement Count (ACH.COUNT$_{act}$) is incremented, and the right-side generally corresponds to the logic associated with $S_2$ by which its Achievement Count (ACH.COUNT$_{press}$) is incremented.

At blocks 310A and 310B, an STR associated with each sensor is calculated using Equations 2 and 3 hereinabove described in Part IV.

At blocks 312A and 312B, a determination is made as to whether the Achievement Criterion (ACH.CRITERION) has been met for each sensor. In particular, the STR associated with each sensor is compared with the ACH.CRITERION established for such sensor, to determine whether the STR has exceeded a threshold rate (Achievement Rate) for a predetermined time interval (Achievement Duration), and if so, the sensor's respective ACH.COUNT is incremented by 1 as shown at blocks 314A and 314B. In the preferred embodiment, since processing logistics of pacemaker 100 involve calculation of each sensor's STR in an alternating fashion, performing one STR calculation every two-second cycle, the Achievement Duration is set at 4 seconds to accommodate this operation. It will be understood, however, that these processing steps can be performed in parallel if desired, and the Achievement Duration can be shorter or longer as a function of such processing considerations.

At blocks 316A and 316B, an SPR associated with each sensor is calculated in a manner hereinabove described, based upon its most current STR and the contribution thereto required using the appropriate attack or decay function (ACT.ATTACK.TC, ACT.DECAY.TC, PRESS.ATTACK.TC and PRESS.DECAY.TC).

At block 318, assuming both sensors are enable, the Optimized Pacing Rate (OPR) which pacemaker 100 will deliver is calculated based upon the current SPR values calculated for each sensor (SPR$_{act}$ and SPR$_{press}$) and the current Weighting Coefficient (COEFF) value for the present Optimization Period, using Equation 1 hereinabove described in Part II.

At block 320, pacemaker 100 determines whether the predetermined time interval associated with the Optimization Period (OPT.PERIOD) has elapsed. If not, pacemaker gathers new RCP-based data samples (i.e., updated ACT.COUNT and PRESS.AVG) shown at block 322, and resumes processing additional cycles in the manner described above. Once OPT.PERIOD has elapsed, pacemaker logic associated with optimization is initiated by exiting this flowchart at exit position B to commence optimization logic shown in FIGS. 4 and 5. In the preferred embodiment, OPT.PERIOD is selected at twenty-four hours, using crystal oscillator 138 which provides a real-time clock function. It will be understood that OPT.PERIOD can be set to be shorter or longer time intervals, if desired. A setting at 24 hours, however, is believed to provide a time interval which is an appropriate length to permit sufficient rate-response related data to be gathered between optimization procedures, while optimizing at a frequency which accommodates most patient's needs, including chronobiologic behaviors such as circadian rhythm. OPT.PERIOD can alternatively be set, for example, to multiples of twenty-four periods for accommodation of variations in patients' behavior, such as infradian rhythms or other factors.

Part VI. Optimization in General

Figure 4:
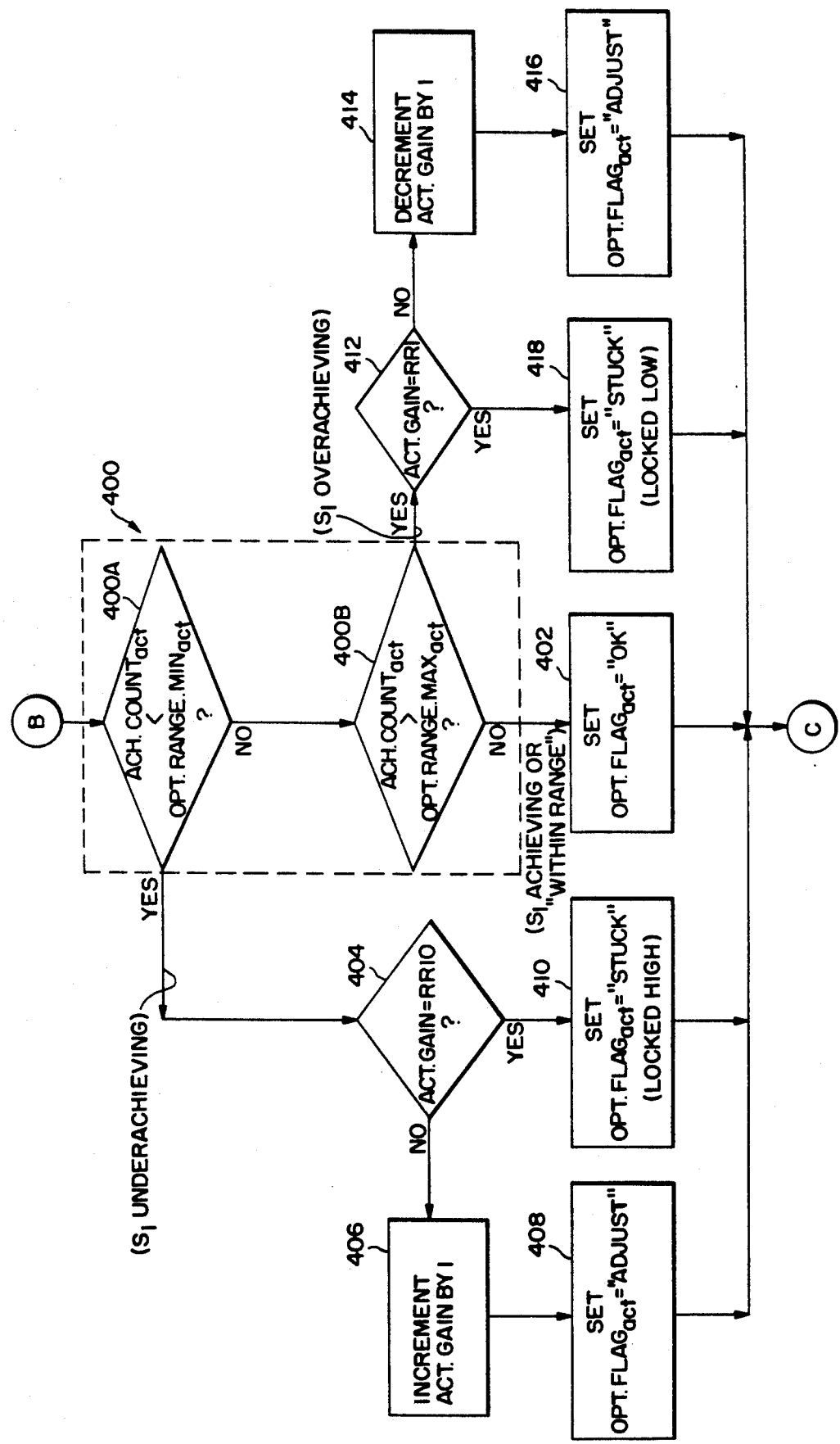
FIG. 4 is a simplified flowchart showing the basic function of software of the pacemaker of FIG. 1 for varying a sensor's rate response or gain as a function of its achievement criterion, such that the sensor's gain is automatically adjusted for purposes of deriving an optimized pacing rate.
Figure 5:
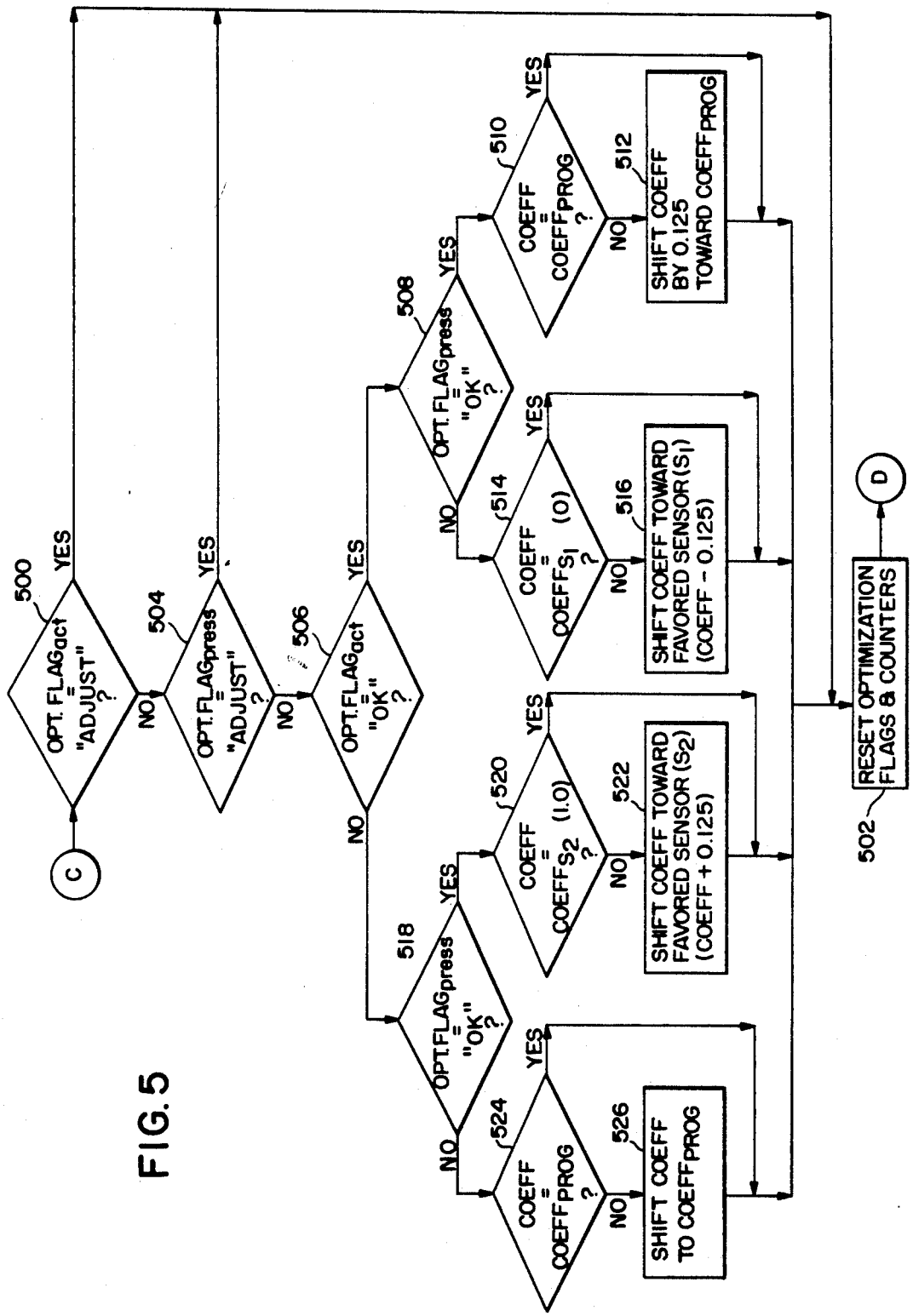
FIG. 5 is a simplified flowchart showing the basic function of software of the pacemaker of FIG 1 for varying a sensor weighting coefficient as a function of each of the sensor's achievement criterion and sensor gain adjustment, such that the relative contribution or weighting given to each sensor's output and target pacing rate is automatically adjusted for purposes of deriving an optimized pacing rate.

FIGS. 4 and 5 are simplified flowcharts showing the basic function of software for performing optimization according to the present invention, for purposes of optimizing the rate of stimulus pulses (Optimized Pacing Rate or "OPR") being provided by pacemaker 100.

FIG. 4 relates to a sensor gain optimization procedure, useful in the context of a single or a multiple sensor-driven rate-responsive pacemaker, wherein a sensor's rate response or gain is varied as a function of its Achievement Criterion.

FIG. 5 relates to a sensor weighting optimization procedure, useful in the context of a multiple sensor-driven, rate-responsive pacemaker, wherein a sensor weighting coefficient (Weighting Coefficient or "COEFF") is varied as function of the rate response or gain adjustments which were made (i.e., varied from RR1 to RR10), if possible, for each sensor during the sensor gain optimization procedure. Thus, the Weighting Coefficient (COEFF) is varied as a function of the Achievement Criterion for each of the sensors, such that the proportion or weight of control given to each sensor's output is regulated appropriately for purposes of deriving an Optimized Pacing Rate for the patient.

The overall control logic of optimization according to the present invention, described in the simplified context of a two-sensor application, can be summarized as follows:

A. General Rules for Optimization (1) The Optimization Range (OPT.RANGE) for each sensor is defined by a minimum value (OPT.RANGE.MIN) and a maximum value (OPT.RANGE.MAX). At the end of each Optimization Period (OPT.PERIOD), during each optimization cycle, the Achievement Count (ACH.COUNT) for each sensor is compared to its respective OPT- .RANGE. Based upon such comparison, a sensor gain optimization (adjusting each sensor's rate response or gain (ACT.GAIN or PRESS.GAIN)) and/or a sensor weighting optimization (adjusting a Weighting Coefficient (COEFF) are performed, if appropriate, by pacemaker 100 at the end of each OPT.PERIOD.

(2) A sensor gain is characterized as "underachieving" if its ACH.COUNT is less than the OPT.RANGE.MIN.

(3) A sensor gain is characterized as "overachieving" if its ACH.COUNT is greater than the OPT.RANGE.MAX.

(4) A sensor gain is characterized as "within range" or "achieving its criteria" if its ACH.COUNT is greater than or equal to its OPT.RANGE.MIN and less than or equal to its OPT.RANGE.MAX.

(5) A sensor gain is characterized as at "minimum gain" if it is set at its lowest available rate response setting (shown, for example, as RR1 in FIGS. 2A and 2B).

(6) A sensor gain is characterized as at "maximum gain" if it is set at its highest available rate response setting (shown, for example, as RR10 in FIGS. 2A and 2B).

(7) A sensor gain is characterized as "locked low" or "stuck" if, during the current optimization cycle, it is desired to decrease the sensor gain but it is already set at its lowest available rate response setting (e.g., RR1) due to an adjustment from a previous optimization cycle.

(8) A sensor gain is characterized as "locked high" or "stuck" if, during the current optimization cycle, it is desired to increase the sensor gain but it is already set at its highest available rate response setting (e.g., RR10) due to an adjustment from a previous optimization cycle.

(9) Adjustments to sensor gain (RR) are made in step increments or decrements of one setting at a time per optimization cycle (e.g., from RR3 to RR4).

(10) Adjustments to Weighting Coefficient (COEFF) are generally made in single step increments or decrements of 0.125 per optimization cycle based upon certain conditions encountered as specified below for the sensor weighting optimization procedure. A Programmed Coefficient Value (COEFF$_{PROG}$) is programmed during initialization with a desired value which will be used as an initial COEFF value for the first optimization procedure. Under certain conditions encountered during sensor weighting optimization as specified hereinbelow, the COEFF will be set to the COEFF$_{PROG}$, or be shifted toward the COEFF$_{PROG}$ in increments, in single steps.

(11) In the preferred embodiment having two sensors, for example, a single Weighting Coefficient (COEFF) is used according to Equation 1 hereinabove described and repeated below for convenience of the reader as follows:

$$OPR = [(1 - COEFF)*SPR_{act}] + (COEFF*SPR_{press}).$$

Thus, a simple means for adjusting the weight multiplier or "sensor coefficient" for each Sensor Pacing Rate (SPR) is provided, wherein the weight SPR$_{act}$ is given varies inversely with respect to the weight SPR$_{press}$ is given, as the COEFF is adjusted. Thus, for any COEFF value ranging from 0 to 1, the equivalent "sensor coefficient" for each SPR is as follows:

| SPR type | "sensor coefficient" value |
| --- | --- |
| SPR$_{act}$ | value = (1 − COEFF) |
| SPR$_{press}$ | value = COEFF |

Therefore, making an adjustment in the COEFF such that a particular selected or favored sensor's SPR will be given greater weight or emphasis than the other sensor's SPR (i.e., the selected sensor's "sensor coefficient" will be increased and the other sensor's "sensor coefficient" will be decreased) is characterized as "shifting the COEFF toward the favored sensor". In the preferred embodiment, for example, "shifting the COEFF toward the favored sensor" requires the following adjustment in the COEFF:

| Favored Sensor (SPR type) | COEFF Adjustment |
| --- | --- |
| S$_1$ (SPR$_{act}$) | Decrement COEFF |
| S$_2$ (SPR$_{press}$) | Increment COEFF. |

Consequently, a COEFF value of 0 will most heavily favor the weighting for S$_1$ (COEFF$_{S1}$), and a COEFF value of 1.0 will most heavily favor the weighting for S$_2$ (COEFF$_{S2}$).

(12) An Optimization Flag (OPT.FLAG) corresponding to each sensor (e.g., OPT.FLAG$_{act}$ and OPT.FLAG$_{press}$) is used to provide an indication of optimization activity taken with respect to sensor gain optimization for each sensor. OPT.FLAG can be set to three different values (e.g., 1, 2 or 3) which correspond to three conditions ("OK", "ADJUSTED" or "STUCK") identifying the type of optimization activity taken:

| Condition | Optimization Activity |
| --- | --- |
| "OK" | Gain adjustment not needed and not made (since ACT.COUNT is within OPT.RANGE). |
| "ADJUSTED" | Gain was adjusted by increment or decrement (required since ACT.COUNT is outside of OPT.RANGE). |
| "STUCK" | Gain adjustment was needed but could not be made (although ACT.COUNT was outside of OPT.RANGE, sensor gain was locked high or locked low). |

B. Rules for Sensor Gain Optimization (1) If a sensor is within range, its sensor gain will not be adjusted.

(2) If a sensor is overachieving and its gain is not at minimum gain, its gain will be decreased one setting.

(3) If a sensor is underachieving and its gain is not at maximum gain, its gain will be increased one setting.

(4) Gain for both sensors can be changed each optimization cycle if conditions B(2) or B(3) exist.

(5) If a sensor is overachieving and its sensor gain is already set at minimum (i.e., stuck in a locked low condition), then its sensor gain cannot be decreased further, and no sensor gain adjustment will be made.

(6) If a sensor is underachieving and its gain is already set at maximum gain (i.e., stuck in a locked high condition), then its sensor gain cannot be increased further, and no sensor gain adjustment will be made.

C. Rules for Sensor Weighting Optimization (1) If a sensor's gain is adjusted in an optimization cycle, no adjustment in that sensor's "sensor coefficient" will be made during that optimization cycle (i.e., no adjustment to the COEFF value will be made during that cycle). Thus, in the preferred embodiment, when only one sensor's gain is adjusted, regardless of the gain optimization activity for the other sensor, no adjustment in weighting will be performed during that cycle.

(2) If both sensor gains are adjusted in an optimization cycle, no adjustment in weighting will be made during that optimization cycle (i.e., no adjustment to the COEFF value will be made during that cycle).

(3) If both sensors are within range (i.e., achieving their criteria), regardless of their gain settings, the weighting coefficient is adjusted one setting from its current COEFF value (i.e., a single step increment or decrement of 0.125) toward the Programmed Coefficient Value ($COEFF_{PROG}$).

(4) If both sensors are underachieving and both sensor gains are already set at maximum gain (i.e., both sensor gains are stuck in a locked high condition), the COEFF is shifted from its current value to the $COEFF_{PROG}$ in a single adjustment.

(5) If both sensors are overachieving and both sensor gains are already set at minimum gain (i.e., both sensor gains are stuck in a locked low condition), the COEFF is shifted from its current value to the $COEFF_{PROG}$ in a single adjustment.

(6) If one of the sensors is overachieving and its sensor gain is already set at minimum gain (i.e., its sensor gain is stuck in a locked low condition), and the other sensor is underachieving and its sensor gain is already set at maximum gain (i.e., its sensor gain is stuck in a locked high condition), the COEFF is shifted from its current value to the $COEFF_{PROG}$ in a single adjustment.

(7) If one of the sensors is underachieving and its sensor gain is set at maximum (i.e., its sensor gain is stuck in a locked high condition) and the other sensor is within range, then the sensor which is within range is be characterized as the "favored sensor" and the other sensor whose sensor gain is stuck is characterized as the "stuck sensor". In this situation, the COEFF is adjusted one setting from its current COEFF value (i.e., a single step increment or decrement of 0.125), by "shifting toward the favored sensor" (i.e., the favored sensor's SPR will be given greater weight or emphasis than the stuck sensor's SPR).

(8) If one of the sensors is overachieving and its sensor gain is set at minimum (i.e., its sensor gain is stuck in a locked low condition) and the other sensor is within range, then the sensor which is within range is be characterized as the "favored sensor" and the other sensor whose sensor gain is stuck is characterized as the "stuck sensor". In this situation, the COEFF is adjusted one setting from its current COEFF value (i.e., a single step increment or decrement of 0.125), by "shifting toward the favored sensor" (i.e., the favored sensor's SPR will be given greater weight or emphasis than the stuck sensor's SPR).

Part VII. Sensor Gain Optimization Procedure

FIGS 4 illustrates the basic function of software for performing optimization of sensor gain, according to the present invention. For ease of explanation, sensor gain optimization logic is shown for one sensor only, using the activity (first) sensor $S_1$ for this example. It will be understood, however, that the software logic described in FIG. 4 is applicable to pacemakers having one, two, or more sensors, for which an optimization of sensor rate response or gain as a function of an Achievement Criterion is desired, and the logic is essentially identical for each sensor gain being optimized (e.g., for optimizing PRESS.GAIN for the second sensor $S_2$).

Entering the flowchart at starting position B, a determination is made at composite block, shown by dashed lines at 400, as to whether the sensor's Achievement Count ($ACH.COUNT_{act}$) is "within range" of its Optimization Range ($OPT.RANGE_{act}$), namely, whether $OPT.RANGE.MIN_{act} \geq ACH.COUNT._{act} \leq OPT.RANGE.MAX_{act}$. A determination that $ACH.COUNT_{act}$ was "within range" for the twenty-four hour Optimization Period (OPT.PERIOD) which has just elapsed is indicative that the sensor's gain (ACT.GAIN) or rate response setting (RR) was appropriate for the patient's needs, and no sensor gain adjustment is necessary for gain optimization.

A determination is first made at block 400A as to whether the activity sensor was underachieving, namely, whether its Achievement Count is below its Optimization Range (i.e., whether $ACT.COUNT_{act} < OPT.RANGE.MIN_{act}$). A decision of NO at block 400A results if the sensor was not underachieving (i.e., $ACT.GAIN \geq OPT.RANGE.MIN_{act}$). Consequently, a determination is then made at block 400B as to whether the activity was overachieving, namely, whether its Achievement Count is above its Optimization Range (i.e., whether $ACT.COUNT_{act} > OPT.RANGE.MAX_{act}$). A decision of NO at block 400B results if the sensor was not overachieving (i.e., $ACT.GAIN \leq OPT.RANGE.MAX_{act}$). Under these conditions, no sensor gain adjustment is required, and the Optimization Flag ($OPT.FLAG_{act}$) is set at block 402 to "OK" status, followed by exiting this flowchart at exit position C to commence the sensor weighting optimization logic shown in FIG. 5.

A determination, however, at composite block 400 that the sensor's Achievement Count ($ACH.COUNT_{act}$), is not "within range" of its Optimization Range ($OPT.RANGE_{act}$) being used for the Optimization Period (OPT.PERIOD) which has just elapsed (i.e., the sensor was either underachieving or overachieving), will cause pacemaker 100 to perform the remainder of optimization logic shown in FIG. 4. A determination that the Achievement Count is not "within range" indicates that the sensor gain was not set to optimally meet the needs of the patient over the previous Optimization Period which has just elapsed (i.e., ACT.GAIN should be incremented or decremented for the next Optimization Period, since sensor $S_1$ was either overachieving or underachieving its Achievement Criterion). The objective, therefore, of this optimization logic will be to cause, if possible, an adjustment to be made to the sensor gain (increment or decrement). The gain adjustment will be made by pacemaker 100 in such a manner that the sensor's Achievement Count developed during the next Optimization Period will be more likely to fall "within range" of its Optimization Range. Consequently, the activity-driven, rate response behavior of pacemaker 100 will be optimzied as a function of the Achievement Criterion for the activity sensor.

Returning to composite block 400, a decision of YES results at block 400A if sensor $S_1$ was underachieving (i.e., $ACT.COUNT_{act} < OPT.RANGE.MIN_{act}$). To provide a desired gain optimization in response to such detected underachievement, a determination is then made at block 404 as to whether the sensor gain (ACT.GAIN) is "stuck", or alternatively, whether it can be increased. A decision of NO results at block 404 if the current gain setting is not already set at its highest available sensor gain or rate response setting (i.e., NO if ACT.GAIN is not stuck in locked high condition which corresponds to the "maximum gain" of RR10 as shown in FIG. 2A in the preferred embodiment). Consequently, the sensor gain will be incremented one setting (e.g., from RR5 to RR6) at block 406 by means of pacemaker 100 performing calculations which modify variables A, B, C and D to derive an adjusted rate response function. The Optimization Flat ($OPT.GAIN_{act}$) is set at block 408 to "ADJUSTED" status, followed by exiting this flowchart at exit position C to commence the sensor weighting optimization logic shown in FIG. 5.

Conversely, a decision of YES results at block 404 if the current gain setting is already set at its highest available sensor gain or rate response setting (i.e., YES if ACT.GAIN=RR10). Therefore, ACT.GAIN is locked high and no further increase in sensor gain can be performed. Consequently, the Optimization Flag ($OPT.GAIN_{act}$) is set at block 410 to "STUCK" status, followed by exiting this flowchart at exit position C to commence the sensor weighting optimization logic shown in FIG. 5.

Returning again to composite block 400, a decision of YES results at block 400B is sensor $S_1$ was overachieving (i.e., $ACT.COUNT_{act} > OPT.RANGE.MAX_{act}$). To provide a desired gain optimization in response to such detected overachievement, a determination is then made at block 412 as to whether the sensor gain (ACT.GAIN) is "stuck", or alternatively, whether it can be decreased. A decision of NO results at block 412 if the current gain setting is not already set at its lowest available sensor gain or rate response setting (i.e., NO if ACT.GAIN is not stuck in locked low condition which corresponds to the "minimum gain" of RR1 as shown in FIG. 2A in the preferred embodiment). Consequently, the sensor gain will be decremented one setting (e.g., from RR5 to RR4) at block 414 by means of pacemaker 100 performing calculations which modify variables A, B, C and D to derive an adjusted rate response function. The Optimization Flag ($OPT.GAIN_{act}$) is set at block 416 to "ADJUSTED" status, followed by exiting this flowchart at exit position C to commence the sensor weighting optimization logic shown in FIG. 5.

Conversely, a decision of YES results at block 412 if the current gain setting is already set at its lowest available sensor gain or rate response setting (i.e., YES if ACT.GAIN=RR1). Therefore, ACT.GAIN is locked low and no further decrease in sensor gain can be performed. Consequently, the Optimization Flag ($OPT.GAIN_{act}$) is set at block 418 to "STUCK" status, followed by exiting this flowchart at exit position C to commence the sensor weighting optimization logic shown in FIG. 5.

It will be understood that the same sensor gain optimization logic shown in FIG. 4 will also be performed for the second sensor $S_2$, commencing at starting position B and, concluding at exit position C, to provide the appropriate adjustment, if possible, to the pressure sensor's gain (PRESS.GAIN).

It will also be understood by those skilled in the art that the particular technique by which the foregoing sensor gain is adjusted for optimization is not critical, and that several alternatives are available. Some alternatives which are regarded as functional equivalents to the specific type of sensor gain adjustment described above can include, for example: (1) selectively adjusting the threshold for sensor output (e.g., ACT.THRESH); (2) selectively adjusting the sensor's amplification of the raw sensor signal; or (3) selectively adjusting the sensor output value mathematically by means of a range of output multiplier values.

Part VIII. Sensor Weighting Optimization Procedure

FIG. 5 illustrates the basic function of software for performing optimization of sensor Weighting Coefficient (COEFF), according to the present invention. At the end of each Optimization Period, following the sensor gain optimization procedure described in FIG. 4, the sensor weighting optimization procedure will be performed. The objective of this optimization logic will be to cause, if possible, the Weighting Coefficient to be varied as function of the rate response or gain adjustments which were made, if possible, for each sensor during the sensor gain optimization procedure. Thus, the Weighting Coefficient (COEFF) is varied as a function of the Achievement Criterion for each of the sensors, such that the proportion or weight of control given to each sensor's output is regulated appropriately for purposes of deriving an Optimized Pacing Rate for the patient.

Upon entering the flowchart at starting position C, the Optimization Flag for activity sensor $S_1$ ($OPT.FLAG_{act}$) and the Optimization Flag for pressure sensor $S_2$ ($OPT.FLAG_{press}$) will have been set to their respective values which correspond to the optimization activity performed during the sensor gain optimization cycle described in FIG. 4 (e.g., OPT.FLAG="OK", "ADJUSTED" or "STUCK"). Adjustments made in the sensor weighting optimization procedure will be made based upon the respective values for each of these Optimization Flags, according to the logic rules hereinabove described in Part VI.

A determination is made at block 500 as to whether the gain for $S_1$ was adjusted. A decision of YES at block 500 results if the first sensor's rate response (ACT.GAIN) was adjusted (i.e., Yes if $OPT.FLAG_{act}$="ADJUSTED"). At this point, therefore, $OPT.FLAG_{act}$="ADJUSTED", and $OPT.FLAG_{press}$ corresponds to either "OK", "ADJUSTED" or "STUCK". Under this condition, no adjustment to the Weighting Coefficient is necessary. Before exiting this flowchart at exit position D to commence another Optimization Period, however, the various registers associated with providing the flagging, counting and timing functions for the sensor gain and sensor weighting optimization procedures, such as for setting the Optimization Flags and timing the Optimization Period, are reset to the appropriate starting values at block 502.

A decision of NO at block 500 results if the first sensor's rate response (ACT.GAIN) was not adjusted during the sensor gain optimization procedure. At this point, therefore, OPT.FLAG$_{act}$ corresponds to either "OK" or "STUCK", and OPT.FLAG$_{press}$ corresponds to either "OK", "ADJUSTED" or "STUCK".

A determination is then made at block 504 as to whether the gain for S$_2$ was adjusted. A decision of YES at block 504 results if the second sensor's rate response (PRESS.GAIN) was adjusted (i.e., Yes if OPT.FLAG$_{press}$="ADJUSTED"). At this point, therefore, OPT.FLAG$_{act}$ corresponds to either "OK" or "STUCK", and OPT.FLAG$_{press}$="ADJUSTED". Under this condition, no adjustment to the Weighting Coefficient is necessary. Therefore, appropriate resetting functions at block 502 are performed, followed by exiting this flowchart at exit position D to commence another Optimization Period.

A decision of NO at block 504 results if the second sensor's rate response (PRESS.GAIN) was not adjusted during the sensor gain optimization procedure. At this point, therefore, OPT.FLAG$_{act}$ corresponds to either "OK" or "STUCK", and OPT.FLAG$_{press}$ corresponds to either "OK" or "STUCK".

A determination is then made at block 506 as to which of the two remaining situations account for the absence of a gain adjustment for S$_1$, namely, whether OPT.FLAG$_{act}$ corresponds to "OK" or "STUCK". The specific test used is whether OPT.FLAG$_{act}$ corresponds to "OK".

A decision of YES at block 506 results if the non-adjustment was due to the fact that S$_1$ was achieving its Achievement Criterion, namely, that its ACT.COUNT$_{act}$ was "within range" of its OPT.RANGE$_{act}$ (i.e., YES if OPT.FLAG$_{act}$ corresponds to "OK"). At this point, therefore, OPT.FLAG$_{act}$ corresponds to "OK", and OPT.FLAG$_{press}$ corresponds to either "OK" or "STUCK".

Following a decision of YES at block 506, a determination is then made at block 508 as to which of the two remaining situations account for the absence of a gain adjustment for S$_2$, namely, whether OPT.FLAG$_{press}$ corresponds to "OK" or "STUCK". The specific test used is whether OPT.FLAG$_{press}$ corresponds to "OK".

A decision of YES at block 508 results if the non-adjustment was due to the face that S$_2$ was achieving its Achievement Criterion, namely, that its ACH.COUNT$_{press}$ was "within range" of its OPT.RANGE$_{press}$ (i.e., YES if OPT.FLAG$_{press}$ corresponds to "OK"). At this point, therefore, OPT.FLAG$_{act}$ and OPT.FLAG$_{press}$ both correspond to "OK". Under this condition, it is desirable to adjust the current COEFF value toward the COEFF$_{PROG}$ in a single step increment or decrement of 0.125. A determination is first made at block 510 as to whether the Weighting Coefficient (COEFF) is already set at its Programmed Coefficient Value (COEFF$_{PROG}$). If a decision of YES at block 510 results, no adjustment to COEFF is necessary. Therefore, appropriate resetting functions at block 520 are performed, followed by exiting this flowchart at exit position D to commence another Optimization Period. A decision of NO at block 510 requires the current COEFF value be adjusted at block 512 toward the COEFF$_{PROG}$ in a single step increment or decrement of 0.125, followed by resetting functions at block 502 and exiting at D to commence another Optimization Period.

Returning again to block 508, a decision of NO results at block 508 if the non-adjustment was due to the fact that S$_2$ was failing to achieve its Achievement Criterion and its desired gain adjustment could not be made because it was stuck in locked high condition (i.e., RR10 while underachieving) or it was stuck in locked low condition (i.e., RR1 while overachieving) (i.e., NO if OPT.FLAG$_{press}$ corresponds to "STUCK"). At this point, therefore, OPT.FLAG$_{act}$ corresponds to "OK", and OPT.FLAG$_{press}$ corresponds to "STUCK". In this situation, S$_1$ is considered the "favored sensor" and S$_2$ is considered the "stuck sensor". Under this condition, it is desirable to shift the COEFF toward the favored sensor, such that the Sensor Pacing Rate for the favored sensor (SPR$_{act}$) is given greater weight or emphasis than that of the stuck sensor (SPR$_{press}$) for purposes of deriving the Optimized Pacing Rate (OPR) according to Equation 1 hereinabove set forth in Part II. This is accomplished by shifting from the current COEFF value toward a COEFF value which will most heavily favor the weighting for S$_1$. In the preferred embodiment, the limit to which COEFF can be shifted to most heavily weight SPR$_{act}$ is a COEFF setting of 0 (such limit referred to as COEFF$_{S1}$). A determination is first made at block 514, therefore, as to whether the COEFF is already set at COEFF$_{S1}$. If a decision of YES at block 514 results, no adjustment to COEFF is necessary. Therefore, appropriate resetting functions at block 502 are performed, followed by exiting this flowchart at exit position D to commence another Optimization Period. If a decision of No at block 514 results, the current COEFF value is adjusted at block 516 toward the favored sensor (i.e., adjust the COEFF value toward its limit of COEFF$_{S1}$) in a single step decrement of 0.125, followed by resetting functions at block 502 and exiting at D to commence another Optimization Period.

Returning again to block 506, a decision of NO at block 506 results if the non-adjustment was due to the fact that S$_1$ was failing to achieve its Achievement Criterion and its desired gain adjustment could not be made because it was stuck in locked high condition (i.e., RR10 while underachieving) or it was stuck in locked low condition (i.e., RR1 while overachieving) ((i.e., NO if OPT.FLAG$_{act}$ corresponds to "STUCK"). At this point, therefore, OPT.FLAG$_{act}$ corresponds to "STUCK", and OPT.FLAG$_{press}$ corresponds to either "OK" or "STUCK".

Following a decision of NO at block 506, a determination is then made at block 518 as to which of the two remaining situations account for the absence of a gain adjustment for S$_2$, namely, whether OPT.FLAG$_{press}$ corresponds to "OK" or "STUCK". The specific test used is whether OPT.FLAG$_{press}$ corresponds to "OK".

A decision of YES at block 518 results if the non-adjustment was due to the fact that S$_2$ was achieving its Achievement Criterion, namely, that its ACH.COUNT$_{press}$ was "within range" of its OPT.RANGE$_{press}$ (i.e., YES if OPT.FLAG$_{press}$ corresponds to "OK"). At this point, therefore, OPT.FLAG$_{act}$ corresponds to "STUCK", and OPT.FLAG$_{press}$ corresponds to "OK". In this situation, S$_2$ is considered the "favored sensor" and S$_1$ is considered the "stuck sensor". Under this condition, it is desirable to shift the COEFF toward the favored sensor, such that the Sensor Pacing Rate for the favored sensor (SPR$_{press}$) is given greater weight or emphasis than that of the stuck sensor (SPR$_{act}$) for purposes of deriving the Optimized Pacing Rate (OPR) according to Equation 1 hereinabove set forth in Part II. This is accomplished by shifting from the current COEFF value toward a COEFF value which will most heavily favor the weighting for $S_2$. In the preferred embodiment, the limit to which COEFF can be shifted to most heavily weight $SPR_{press}$ is a COEFF setting of 1.0 (such limit referred to as $COEFF_{S2}$). A determination is first made at block 520, therefore, as to whether the COEFF is already set at $COEFF_{S2}$. If a decision of YES at block 520 results, no adjustment to COEFF is necessary. Therefore, appropriate resetting functions at block 520 are performed, followed by exiting this flowchart at exit position D to commence another Optimization Period. If a decision of No at block 520 results, the current COEFF value is adjusted at block 522 toward the favored sensor (i.e., adjust the COEFF value toward its limit of $COEFF_{S1}$) in a single step increment of 0.125, followed by resetting functions at block 502 and exiting at D to commence another Optimization Period.

Returning again to block 518, a decision of NO at block 518 results if the non-adjustment was due to the fact that $S_2$ was failing to meet it Achievement Criterion and its desired gain adjustment could not be made because it was stuck in locked high condition (i.e., RR10 while underachieving) or it was stuck in locked low condition (i.e., RR1 while overachieving), (i.e., NO if $OPT.FLAG_{press}$ corresponds to "STUCK"). At this point, therefore, $OPT.FLAG_{act}$ and $OPT.FLAG_{press}$ both correspond to "STUCK". Under this condition, it is desirable to adjust the COEFF from its current value to the $COEFF_{PROG}$ in a single adjustment. For example, if $COEFF_{PROG}$ is programmed at 0.500 and the current value of COEFF is 0.750, then a single adjustment decrementing COEFF by 0.250 to the programmed value of 0.500 would be made. A determination is first made at block 524 as to whether the current value of the Weighting Coefficient (COEFF) is already set at its Programmed Coefficient Value ($COEFF_{PROG}$). If a decision of YES at block 524 results, no adjustment to COEFF is necessary. Therefore, appropriate resetting functions at block 502 are performed, followed by exiting this flowchart at exit position D to commence another Optimization Period. A decision of NO at block 524 requires the current COEFF value be adjusted at block 526 from it current COEFF value to the $COEFF_{PROG}$ in a single adjustment, followed by resetting functions at block 502 and exiting at D to commence another Optimization Period.

Thus, it can be appreciated that the present invention provides a very flexible means for optimization of rate responsiveness in a pacemaker, while offering simplicity of implementation. It will be apparent to those skilled in the art, for example, that the sensor gain optimization procedure can be practiced separately from the sensor weighting optimization procedure, each of which can be varied as a function of their own selected achievement criterion. It will also be appreciated by those skilled in the art that the use of a sensor weighting value, whether a predetermined value or an adjustable parameter, may be used for purposes of combining such sensor-determined pacing rates without using an optimization procedure, if desired, and will yield substantial performance benefits of its own accord.

The self-adapting rate optimization behavior provided by the optimization procedures of the present invention are believed, for example, to minimize most difficulties ordinarily associated with combining sensors which sense different rate control parameters, such difficulties including differences in (1) long-term stability; (2) immunity to noise; (3) response time to changing metabolic conditions; and (4) correlation between sensor output and the rate control parameter being measured (i.e., variations in linearity). Consequently, the present invention introduces greater freedom of choice to the clinician with respect to the types of sensors which may be used therewith.

Selecting rate control parameters which have highly complementary characteristics is not necessarily required. In fact, the present invention can be practiced, for example, with sensors having less rapid onset of detected metabolic change than those described herein. Other sensor combinations might include, for example, one sensor to determine timing and the other the magnitude of response. As another example, sensors having maximum sensitivity at different levels of exertion might be used.

While the invention has been described above in connection with the particular embodiments and examples, one skilled in the art will appreciate that the invention is not necessarily so limited. It will thus be understood that numerous other embodiments, examples, uses, modifications of, and departures from the teachings disclosed may be made, without departing from the scope of the present invention as claimed herein.

What is claimed is:

1. A rate responsive cardiac pacemaker for providing an optimized pacing rate of stimulation pulses as a function of at least one selected rate control parameter, each of said rate control parameters having a value which varies as a function of changes in a patient's physiologic demand, comprising:
   (A) sensor means for sensing each of said rate control parameter values and for providing a sensor output representative thereof;
   (B) control means coupled to each of said sensor means, comprising:
      (1) rate response defining means for deriving desired pacing rates for each of said sensor means as a function of said sensor output corresponding thereto, to define a predetermined rate response function for each of said sensor means, such that for a predetermined change in sensor output for each of said sensor means a corresponding change in said desired pacing rate is provided;
      (2) achievement monitoring means having a predetermined achievement criterion for each of said sensor means, for monitoring the relationship between each of said derived desired pacing rates and said achievement criterion corresponding thereto over a predetermined optimization period, and for providing an achievement output indicative of each of said monitored relationship, wherein each of said achievement criterion is reflective of expected levels of exercise of said patient during said optimization period;
      (3) output means for providing optimized pacing rates as a function of each of said derived desired pacing rates; and
      (4) rate response control means for adjusting each of said rate response functions, for at least a portion of a subsequent optimization period, as a function of said achievement output corresponding thereto, such that each of said adjusted rate response functions provides an increased or decreased change in desired pacing rate corresponding to said predetermined change in sensor output for each of said sensor means.

2. A rate responsive cardiac pacemaker for providing an optimized pacing rate of stimulation pulses as a function of at least two selected rate control parameters, each of said rate control parameters having a value which varies as a function of changes in a patient's physiologic demand, comprising:

(A) sensor means for sensing each of said rate control parameter values and for providing a sensor output representative thereof;

(B) control means coupled to each of said sensor means, comprising:

(1) rate response defining means for deriving desired pacing rates for each of said sensor means as a function of said sensor output corresponding thereto, to define a predetermined rate response function for each of said sensor means, such that for a predetermined change in sensor output for each of said sensor means a corresponding change in said desired pacing rate is provided;

(2) achievement monitoring means having a predetermined achievement criterion for each of said sensor means, for monitoring the relationship between each of said derived desired pacing rates and said achievement criterion corresponding thereto over a predetermined optimization period, and for providing an achievement output indicative of each of said monitored relationships, wherein each of said achievement criterion is reflective of expected levels of exercise of said patient during said optimization period;

(3) output means for providing optimized pacing rates derived from an adjustable sensor weighting value and each of said desired pacing rates, said sensor weighting value for weighting the relative contribution which each of said desired pacing rates contribute toward said derived optimized pacing rate; and (4) sensor weighting control means, for adjusting said sensor weighting value, for at least a portion of a subsequent optimization period, as a function of each of said achievement outputs.

3. A rate responsive cardiac pacemaker according to claim 2, wherein:

(A) said output means further comprises:

(1) output means for providing optimized pacing rates as a function of each of said derived desired pacing rates;

(B) said control means further comprises:

(1) rate response control means for adjusting each of said rate response functions, for at least a portion of a subsequent optimization period, as a function of said achievement output corresponding thereto, such that each of said adjusted rate response functions provides an increased or decreased change in desired pacing rate corresponding to said predetermined change in sensor output for each of said sensor means; and (C) wherein, said optimized pacing rates are provided as a function of said adjusted rate response functions and said adjusted sensor weighting value.

4. A rate responsive cardiac pacemaker for providing an optimized pacing rate of stimulation pulses as a function of at least two selected rate control parameters, each of said rate control parameters having a value which varies as a function of changes in a patient's physiologic demand, comprising:

(A) sensor means for sensing each of said rate control parameter values and for providing a sensor output representative thereof;

(B) control means coupled to each of said sensor means, comprising:

(1) rate response defining means for deriving desired pacing rates for each of said sensor means as a function of said sensor output corresponding thereto, to define a predetermined rate response function for each of said sensor means, such that for a predetermined change in sensor output for each of said sensor means a corresponding change in said desired pacing rate is provided; and (2) output means for providing optimized pacing rates derived from a predetermined sensor weighting value and each of said desired pacing rates, said sensor weighting value for weighting the relative contribution which each of said desired pacing rates contribute toward said derived optimized pacing rate.

5. A rate responsive cardiac pacemaker according to claim 4, wherein said sensor weighting value is adjustable, and said control means further comprises sensor weighting control means, for adjusting said sensor weighting value.

6. A method for providing an optimized pacing rate of stimulation pulses in a rate responsive cardiac pacemaker, as a function of at least one selected rate control parameter, each of said rate control parameters having a value which varies as a function of changes in a patient's physiologic demand, the method comprising the steps of:

(A) sensing each of said rate control parameter values and providing a sensor output representative thereof;

(B) deriving a desired pacing rate as a function of each of said sensor outputs, thereby defining a predetermined rate response function for each of said sensor outputs which correlates said sensor output with a correspondingly desired pacing rate, such that for a predetermined change in sensor output a corresponding change in said desired pacing rate is provided;

(C) selecting an achievement criterion for each of said sensor outputs which is reflective of expected levels of exercise of said patient over a predetermined optimization period;

(D) monitoring the relationship between each of said derived desired pacing rates and said achievement criterion corresponding thereto over said optimization period, for providing an achievement output indicative of each of said monitored relationship;

(E) providing optimized pacing rates as a function of each of said derived desired pacing rates; and (F) adjusting each of said rate response functions as a function of said achievement output corresponding thereto, such that each of said adjusted rate response functions provides an increased or decreased change in desired pacing rate corresponding to said predetermined change in sensor output.

7. A method for providing an optimized pacing rate of stimulation pulses in a rate responsive cardiac pacemaker, as a function of at least two selected rate control parameters, each of said rate control parameters having a value which varies as a function of changes in a patient's physiologic demand, the method comprising the steps of:

(A) sensing each of said rate control parameter values and providing sensor outputs respectively representative thereof;

(B) deriving a desired pacing rate as a function of each of said sensor outputs, thereby defining a predetermined rate response function for each of said sensor outputs which correlates said sensor output with a correspondingly desired pacing rate, such that for a predetermined change in sensor output a corresponding change in said desired pacing rate is provided;

(C) selecting an achievement criterion for each of said sensor outputs which is reflective of expected levels of exercise of said patient over a predetermined optimization period;

(D) monitoring the relationship between each of said derived desired pacing rates and said achievement criterion corresponding thereto over said optimization period, for providing an achievement output indicative of each of said monitored relationships;

(E) providing optimized pacing rates as a function of each of said derived desired pacing rates by applying an adjustable sensor weighting value to each of said derived desired pacing rates to determine said optimized pacing rates, wherein said sensor weighting value functions for weighting the relative contribution which each of said derived desired pacing rates contributes toward said optimized pacing rates; and (F) adjusting said sensor weighting value, for at least a portion of a subsequent optimization period, as a function of each of said achievement outputs.

* * * * *

UNITED STATES PATENT AND TRADEMARK OFFICE
CERTIFICATE OF CORRECTION

PATENT NO. : 5,154,170
DATED : October 13, 1992
INVENTOR(S) : Tommy D. Bennett, Lucy M. Nichols, Glenn M. Roline, and David L. Thompson It is certified that error appears in the above-identified patent and that said Letters Patent is hereby corrected as shown below:

Column 2, Line 26, delete "packing", and insert in its place --pacing--.

Column 5, Line 62, delete "an don-board", and insert in its place --an on-board--.

Column 6, Line 3, delete "(now shown).", and insert in its place --(not shown).--.

Column 6, Line 11, delete "the n", and insert in its place --then--.

Column 7, Line 28, delete "(AC. CRITERION)", and insert in its place --(ACH. CRITERION).--.

Column 9, Line 16, delete "fist", and insert in its place --first--.

Column 11, Line 35, delete "int he", and insert in its place --in the--.

Column 11, Line 55, delete "is sued", and insert in its place --is used--.

Column 21, Line 24, delete "Flat", and insert in its place --Flag--.

UNITED STATES PATENT AND TRADEMARK OFFICE
CERTIFICATE OF CORRECTION

PATENT NO. : 5,154,170
DATED : October 13, 1992
INVENTOR(S) : Tommy D. Bennett, Lucy M. Nichols, Glenn M. Roline, and David L. Thompson It is certified that error appears in the above-indentified patent and that said Letters Patent is hereby corrected as shown below:

Column 23, Lines 33-34, delete "ACT.COUNT$_{act}$", and insert in its place -- ACH.COUNT$_{act}$--.

Column 23, Line 46, delete "face", and insert in its place --fact--.

Column 23, Line 59, delete "520", and insert in its place --502--.

Column 25, Line 9, delete "520", and insert in its place --502--.

Column 26, Line 52, delete "relationship,", and insert in its place -- relationships,--.

Signed and Sealed this

Twentieth Day of September, 1994

Attest:

BRUCE LEHMAN

Attesting Officer

Commissioner of Patents and Trademarks